(12) United States Patent
Wang

(10) Patent No.: US 10,456,410 B2
(45) Date of Patent: Oct. 29, 2019

(54) HYDROGEN SULFIDE (H2S) RELEASING DONOR COMPOUND FOR DERMAL WOUND REGENERATION

(71) Applicant: University of South Carolina, Columbia, SC (US)

(72) Inventor: Qian Wang, Columbia, SC (US)

(73) Assignee: University of South Carolina, Columbia, SC (US)

( * ) Notice: Subject to any disclaimer, the term of this patent is extended or adjusted under 35 U.S.C. 154(b) by 40 days.

(21) Appl. No.: 15/665,862

(22) Filed: Aug. 1, 2017

(65) Prior Publication Data

US 2019/0038643 A1 Feb. 7, 2019

(51) Int. Cl.
| A61K 31/664 | (2006.01) |
| A61L 15/64 | (2006.01) |
| A61L 15/44 | (2006.01) |
| A61L 15/42 | (2006.01) |
| A61L 15/28 | (2006.01) |
| A61L 15/26 | (2006.01) |

(52) U.S. Cl.
CPC ............ *A61K 31/664* (2013.01); *A61L 15/26* (2013.01); *A61L 15/28* (2013.01); *A61L 15/425* (2013.01); *A61L 15/44* (2013.01); *A61L 15/64* (2013.01); *A61L 2300/10* (2013.01); *A61L 2300/216* (2013.01); *A61L 2400/12* (2013.01); *A61L 2430/34* (2013.01)

(58) Field of Classification Search
CPC ....... A61K 31/664; A61L 15/26; A61L 15/28; A61L 15/425; A61L 15/44; A61L 15/64; A61L 2300/10; A61L 2300/216; A61L 2400/12; A61L 2430/34
See application file for complete search history.

(56) References Cited

U.S. PATENT DOCUMENTS

| 2009/0202617 A1* | 8/2009 | Ward ................... A61K 9/1271 424/447 |
| 2009/0269406 A1* | 10/2009 | Panitch ................. A61K 8/042 424/487 |
| 2011/0165216 A1* | 7/2011 | Chen ...................... A61L 27/14 424/423 |
| 2015/0342969 A1* | 12/2015 | Casola ................. A61K 31/675 514/90 |
| 2017/0253622 A1* | 9/2017 | Xian ..................... C07F 9/4419 |

FOREIGN PATENT DOCUMENTS

WO WO2012/154126 A1 * 11/2012 ............... A61P 35/00

OTHER PUBLICATIONS

Zhang et al. ("Zhang", "A novel pH-controlled hydrogen sulfide donor protects gastric mucosa from aspirin-induced injury", J. Cell. Mol. Med., vol. 21, No. 10, 2017, p. 2441-2451). Published Apr. 7, 2017. (Year: 2017).*

Liu et al. "Hydrogen Sulfide Improves Wound Healing via Restoration of Endothelial Progenitor Cell Functions and Activation fo Angiopoietin-1 in Type 2 Diabetes", Diabetes, vol. 63, May 2014, DOI: 10:2337/db13-0483, pp. 1763-1778. (Year: 2014).*

Szabó, Csaba, and Andreas Papapetropoulos. "Hydrogen sulphide and angiogenesis: mechanisms and applications." British journal of pharmacology 164.3 (2011): 853-865.

Shibuya, Norihiro, et al. "Vascular endothelium expresses 3-mercaptopyruvate sulfurtransferase and produces hydrogen sulfide." The journal of biochemistry 146.5 (2009): 623-626.

Bhatia, Madhav. "Hydrogen sulfide as a vasodilator." IUBMB life 57.9 (2005): 603-606.

Patacchini, Riccardo, et al. "Hydrogen sulfide (H2S) stimulates capsaicin-sensitive primary afferent neurons in the rat urinary bladder." British journal of pharmacology 142.1 (2004): 31-34.

Akter, Farhana "The role of hydrogen sulfide in burns." Burns 42.3 (2016): 519-525.

Wallace, John L., and Rui Wang. "Hydrogen sulfide-based therapeutics: exploiting a unique but ubiquitous gasotransmitter." Nature reviews. Drug discovery 14.5 (2015): 329.

Potente, Michael, Holger Gerhardt, and Peter Carmeliet. "Basic and therapeutic aspects of angiogenesis." Cell 146.6 (2011): 873-887.

Papapetropoulos, Andreas, et al. "Hydrogen sulfide is an endogenous stimulator of angiogenesis." Proceedings of the National Academy of Sciences 106.51 (2009): 21972-21977.

Liu, Fang, et al. "Hydrogen sulfide improves wound healing via restoration of endothelial progenitor cell functions and activation of angiopoietin-1 in type 2 diabetes." Diabetes 63.5 (2014): 1763-1778.

Shen, Yaqi, et al. "Protective effects of hydrogen sulfide in hypoxic human umbilical vein endothelial cells: a possible mitochondria-dependent pathway." International journal of molecular sciences 14.7 (2013): 13093-13108.

Wallace, John L., et al. "Hydrogen sulfide enhances ulcer healing in rats." The FASEB Journal 21.14 (2007): 4070-4076.

Fiorucci, Stefano, et al. "The emerging roles of hydrogen sulfide in the gastrointestinal tract and liver." Gastroenterology 131.1 (2006): 259-271.

Guo, Wei, Ze-yu Cheng, and Yi-zhun Zhu. "Hydrogen sulfide and translational medicine." Acta Pharmacologica Sinica 34.10 (2013): 1284.

Kang, Jianming, et al. "pH-controlled hydrogen sulfide release for myocardial ischemia-reperfusion injury." Journal of the American Chemical Society 138.20 (2016): 6336-6339.

Zhao, Yu, Tyler D. Biggs, and Ming Xian. "Hydrogen sulfide (H 2 S) releasing agents: chemistry and biological applications." Chemical communications 50.80 (2014): 11788-11805.

(Continued)

*Primary Examiner* — Audrea B Coniglio

(74) *Attorney, Agent, or Firm* — Dority & Manning, P.A.

(57) ABSTRACT

A dressing for wound healing is provided, wherein the dressing includes a hydrogen sulfide ($H_2S$) donor compound. The dressing facilitates the delivery of $H_2S$ to a wound site in a controlled manner, which results in an improved wound healing process by stimulating angiogenesis and anti-inflammatory action. In some embodiments, the wound dressing can include an electrospun nanofiber dressing, a sponge dressing, or a hydrogel dressing.

20 Claims, 17 Drawing Sheets

(56) References Cited

OTHER PUBLICATIONS

Li, Ling, et al. "Characterization of a Novel, Water-Soluble Hydrogen Sulfide-Releasing Molecule (GYY4137)." Circulation 117.18 (2008): 2351-2360.
Alexander, Benjamin E., et al. "Investigating the generation of hydrogen sulfide from the phosphonamidodithioate slow-release donor GYY4137." MedChemComm 6.9 (2015): 1649-1655.
Wu, Jiang, et al. "Novel H2S releasing nanofibrous coating for in vivo dermal wound regeneration." ACS applied materials & interfaces 8.41 (2016): 27474-27481.
Lowe, A., et al. "Electrospun nitric oxide releasing bandage with enhanced wound healing." Acta biomaterialia 13 (2015): 121-130.
Teo, Wee E., and Seeram Ramakrishna "A review on electrospinning design and nanofibre assemblies." Nanotechnology 17.14 (2006): R89.
Seo, Song Yi, et al. "Alginate-based composite sponge containing silver nanoparticles synthesized in situ." *Carbohydrate polymers* 90.1 (2012): 109-115.
Lee, Kuen Yong, and David J. Mooney. "Alginate: properties and biomedical applications." Progress in polymer science 37.1 (2012): 106-126.
Jones, Annie, and David Vaughan. "Hydrogel dressings in the management of a variety of wound types: A review." Journal of Orthopaedic nursing 9 (2005): S1-S11.
Kogan, Grigorij, et al. "Hyaluronic acid: a natural biopolymer with a broad range of biomedical and industrial applications." Biotechnology letters 29.1 (2007): 17-25.
Price, Richard D., M. G. Berry, and Harshad A. Navsaria. "Hyaluronic acid: the scientific and clinical evidence." Journal of Plastic, Reconstructive & Aesthetic Surgery 60.10 (2007): 1110-1119.

\* cited by examiner

HYDROGEN SULFIDE (H2S) RELEASING DONOR COMPOUND FOR DERMAL WOUND REGENERATION

BACKGROUND

Hydrogen sulfide ($H_2S$) is a colourless, flammable, water soluble gas, which is recognized exclusively as a toxic gas and environmental hazard. $H_2S$ has been reported as one of three important gasotransmitters together with nitric oxide (NO) and carbon oxide (CO), each of which take part in many physiological and pathological processes. $H_2S$ is also synthesized by mammalian tissues via two pyridoxal-5'-phosphatedependent enzymes responsible for metabolism of L-cysteine: cystathionine beta-synthase (CBS) and cystathionine gamma-lyase (CSE). The endogenous $H_2S$ plays important role in regulating central and peripheral nervous system, cellular metabolism, immunological/inflammatory responses and various aspects of cardiovascular biology. In the cardiovascular system, the principal enzyme involved in the formation of $H_2S$ is CSE, expressed in vascular endothelial cells, smooth muscle cells as well as cardiac myocytes. While in central nervous system, the $H_2S$ was synthesized via CBS. In mammalian tissues and blood, the concentration of $H_2S$ is 1-160 mM under physiological conditions. Higher concentrations of $H_2S$ are present in the brain (50-160 mM) and blood (10-100 mM).

The role of hydrogen sulfide in inflammation, sepsis and burns has been studied recently. The physiological function of $H_2S$ is thought to reduce inflammation and protect tissues from injury (such as ulceration in the gastrointestinal tract), acting through several pathways. $H_2S$ can suppress leukocyte adherence to the vascular endothelium, leukocyte extravasation and consequent formation of oedema. It can substitute for oxygen in driving mitochondrial respiration, thereby attenuating oxidative-stress-related tissue injury. The ability of $H_2S$ to inhibit the activity of phosphodiesterases (PDEs) can contribute to its ability to relax vascular smooth muscle, resulting in enhanced blood flow. Resolution of inflammation can be enhanced by $H_2S$ through actions such as the promotion of neutrophil apoptosis, and driving macrophage differentiation towards the M2 (anti-inflammatory) phenotype. $H_2S$ can modulate the activity of a number of transcription factors: it inhibits nuclear factor-κB (NF-κB), leading to a reduced production of pro-inflammatory cytokines. Increased production of $H_2S$ occurs around sites of damage, such as around ulcers in the gastrointestinal tract, and can accelerate the healing of such damage via the stimulation of angiogenesis.

Angiogenesis is regulated by vascular endothelial growth factor (VEGF) and its signal transduction pathway, which is crucial in the initial stage of wound healing. It is reported that both endogenous and exogenous $H_2S$ can stimulate angiogenesis through PI-2K/Akt pathway and ATP-sensitive potassium channels. The endogenous angiogenic agent VEGF, which promotes elevations in intracellular calcium levels, may lead to $H_2S$ release that in turn contributes to VEGF-stimulated angiogenesis-related properties of ECs. Administration of $H_2S$ to endothelial cells in culture stimulates cell proliferation, migration and tube formation. In addition, administration of $H_2S$ to chicken chorioallantoic membranes stimulates blood vessel growth and branching. Furthermore, in vivo administration of $H_2S$ to mice stimulates angiogenesis and accelerate wound healing in type 2 diabetic mice.

$H_2S$ can protect endothelial cells and promote migration under hypoxic condition in HUVECs. These effects are partially associated with the preservation of mitochondrial function mediated by regulating the mitochondrial-dependent apoptotic pathway. A marked increase in gastric expression of the two key enzymes in hydrogen sulfide synthesis (CBS and CSE) and in hydrogen sulfide synthesis were detected in gastric ulcer in rat. Twice-daily treatment for a week with hydrogen sulfide donors significantly increased the extent of healing of gastric ulcers as compared to vehicle treatment. This study indicated that $H_2S$ is an endogenous regulator of wound healing, and enhancement of endogenous $H_2S$ synthesis or delivery of appropriate concentrations of $H_2S$ may have clinical utility in enhancing the healing of wounds, including gastrointestinal ulcers. $H_2S$ improves wound healing by restoration of EPC functions and activation of Ang-1 in type 2 diabetic mice. The findings indicated that an $H_2S$ donor may lead to novel therapeutic strategies for diabetic vascular complications and diabetic skin ulcerations. In addition, it is proposed that $H_2S$ acts to promote inflammation in the initial period post-injury, but at later stages, $H_2S$ reduces inflammation and improves wound healing in the burn model. Although this action has not yet been extensively studied, it is promising due to the potential therapeutic role of $H_2S$ for treating burns.

Many results indicate that $H_2S$ can improve wound healing due to its functions of stimulating angiogenesis and anti-inflammatory action. Therefore, enhancement of endogenous $H_2S$ synthesis or delivery of appropriate concentrations of $H_2S$ may have clinical utility in enhancing the healing of wounds, including gastrointestinal ulcers. As a gasotransmitter, $H_2S$ rapidly travels through cell membranes without utilizing specific transporters and exerts a host of biological effects on a variety of biological targets resulting in a variety of biological responses. Similarly to the other two gasotransmitters NO and CO, many of the biological responses to $H_2S$ follow a bell-shaped dose-response: the effects of $H_2S$ range from physiological, cytoprotective effects (which occur at low concentrations) to cytotoxic effects (which are generally only apparent at higher concentrations). So far, it is still limited to use $H_2S$ as therapeutic agent in clinic due to shortage of $H_2S$ donors to release $H_2S$ at required concentration controllably and consistently. Therefore, a donor to control the $H_2S$ release process and a system to control the levels of $H_2S$ in different systems in the body is required to ensure that the treatment of burns is not detrimental to other systems.

As such, in order to overcome the limitations of $H_2S$ used in skin dressing clinically, it is necessary to provide donors that can release $H_2S$ consistently and the form of a dressing that can be easily applied over a wound or area of skin.

SUMMARY OF THE INVENTION

In one embodiment of the present invention, a wound dressing is provided. The wound dressing includes a biodegradable scaffold material and a hydrogen sulfide donor.

In one particular embodiment, the hydrogen sulfide donor can include JK-1 having the following structure:

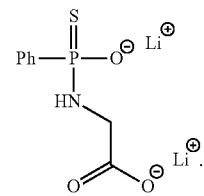

In another embodiment, the wound dressing can release hydrogen sulfide when introduced into an environment having a pH ranging from about 5.0 to about 7.0.

In still another embodiment, the wound dressing can release hydrogen sulfide for a time period of up to 75 hours.

In yet another embodiment, the wound dressing can release hydrogen sulfide at a concentration ranging from about 5 micromolar (μM) to about 50 μM.

In one more embodiment, the biodegradable scaffold material can include a biodegradable polymer, sodium alginate, hyaluronic acid, or a combination thereof. For instance, the biodegradable polymer can include polycaprolactone, polylactic acid, polyglycolic acid, or a combination thereof.

In an additional embodiment, the biodegradable scaffold material can include a nanofibrous scaffold, a sponge, or a hydrogel. Further, the nanofibrous scaffold can be an electrospun nanofibrous scaffold.

In one embodiment, the biodegradable scaffold material can be crosslinked.

In one particular embodiment, the wound dressing can increase the production of CD31 and Ki67 from a wound.

In another embodiment of the present invention, a method of treating a wound is provided. The method includes applying a wound dressing to an area of skin encompassing the wound; and leaving the wound dressing on the area of skin for a time period ranging up to about 75 hours, where the wound dressing comprise a biodegradable scaffold material and a hydrogen sulfide donor.

In one particular embodiment, the hydrogen sulfide donor can include JK-1 having the following structure:

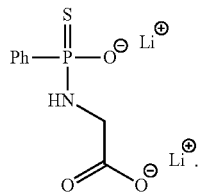

In another embodiment, the wound dressing can release hydrogen sulfide when introduced into an environment having a pH ranging from about 5.0 to about 7.0.

In still another embodiment, the wound dressing can release hydrogen sulfide at a concentration ranging from about 5 micromolar (μM) to about 50 μM.

In yet another embodiment, the biodegradable scaffold material can include a biodegradable polymer, sodium alginate, hyaluronic acid, or a combination thereof. For instance, the biodegradable polymer can include polycaprolactone, polylactic acid, polyglycolic acid, or a combination thereof.

In one more embodiment, the biodegradable scaffold material can include a nanofibrous scaffold, a sponge, or a hydrogel. Further, the nanofibrous scaffold can be an electrospun nanofibrous scaffold.

In an additional embodiment, treating the wound with the wound dressing can increase the production of CD31 and Ki67 from the wound.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1:
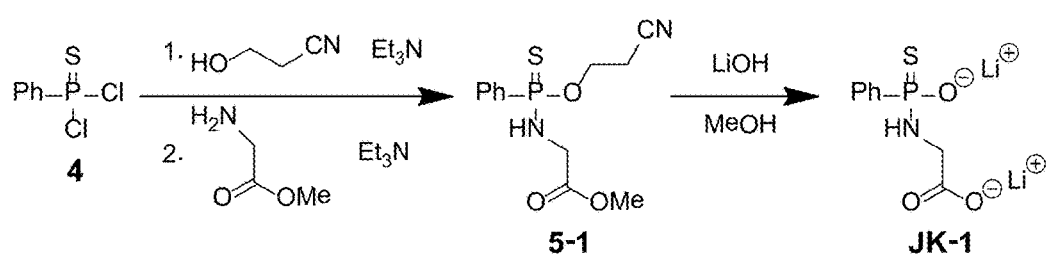
FIG. 1 is a schematic diagram illustrating the synthesis of $H_2S$ donor JK-1.

Repeat use of reference characters in the present specification and drawings is intended to represent the same or analogous features or elements of the present invention.

DEFINITIONS

Chemical elements are discussed in the present disclosure using their common chemical abbreviation, such as commonly found on a periodic table of elements. For example, hydrogen is represented by its common chemical abbreviation H; nitrogen is represented by its common chemical abbreviation N; and so forth.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally, the present invention provides the application of an $H_2S$ donor compound in combination with a wound healing dressing. The wound dressing can be integrated with wound an $H_2S$ donor for releasing $H_2S$ at wound site in a controllable manner in order to improve wound healing process by stimulating angiogenesis and anti-inflammatory action. The wound dressing can include a biodegradable fibrous scaffold, a sponge, a hydrogel, or any other suitable dressing. In one particular embodiment, the fibrous scaffold can be an electropun polycaprolactone nanofiber scaffold. In another embodiment, the sponge can be a sodium alginate sponge. In still another embodiment, the hydrogel can be a hyaluronic acid hydrogel. In any event, an $H_2S$ donor compound such as JK-1 can be incorporated into the dressing and the pH of the dressing and/or the environment in which it is place can be controlled to facilitate the release of $H_2S$ at the wound site in a controlled, sustained manner. JK-1 has the structure as shown in FIG. 1, and, referring to FIG. 1, can be synthesized from phenylphosphonothioic dichloride (4), which can be sequentially treated with 3-hydroxypropionitrile and a C-protected amino acid to provide precursor (5). LiOH-mediated hydrolysis of (5) can then provide the donor product JK-1, which can be prepared with an amino acid (e.g., glycine). Further, although JK-1 is shown in FIG. 1 as the $H_2S$ donor product as formed from glycine, other amino acids (e.g., phenylalanine, valine, alanine, and proline) can be utilized to form other useful $H_2S$ donor products JK-2, JK-3, JK-4, and JK-5 as known in the art. In any event, referring to FIG. 2, at neutral or slightly acidic pH, protonation of phosphonamidothioates should form corresponding phosphorothiols, whereby such process should facilitate the release of $H_2S$ if a nucleophilic carboxylate is presented at a suitable position, where it is thought that the formation of the 5-membered ring product shown in FIG. 2 could be the driving force for $H_2S$ release. The JK-1 $H_2S$ donor product can be incorporated into any suitable biodegradable scaffold material to form a wound dressing, where the $H_2S$ released by the wound dressing can facilitate wound healing by stimulating angiogenesis and anti-inflammatory action as described above.

In one particular embodiment, the hydrogen sulfide ($H_2S$) donor can be incorporated into the biodegradable scaffold material at a concentration ranging from about 0.1 millimolar (mM) to about 150 mM, such as from about 0.5 mM to about 125 mM, such as from about 1 mM to about 100 mM. The $H_2S$ donor can be incorporated into the solution used to form the scaffold, or it can alternatively be applied as a coating after the scaffold is formed. Moreover, regardless of the concentration at which the $H_2S$ donor is incorporated into the biodegradable scaffold, the resulting wound dressing can be applied to any wound, where the environment in which the wound dressing is placed has a pH ranging from about 5.0 to about 7.0, such as from about 5.5 to about 6.9, such as from about 6.0 to about 6.8, wherein the presence of an acidic environment can enable the controlled release of $H_2S$ from the wound dressing to promote healing of the wound, where the lower the pH, the faster the $H_2S$ release from the wound dressing.

As mentioned above, the $H_2S$ donor can be incorporated into a biodegradable scaffold material that can include a biodegradable polymer, sodium alginate, hyaluronic acid, or a combination thereof, where the scaffold material can be a nanofibrous scaffold, a sponge, a hydrogel, etc.

Figure 3:
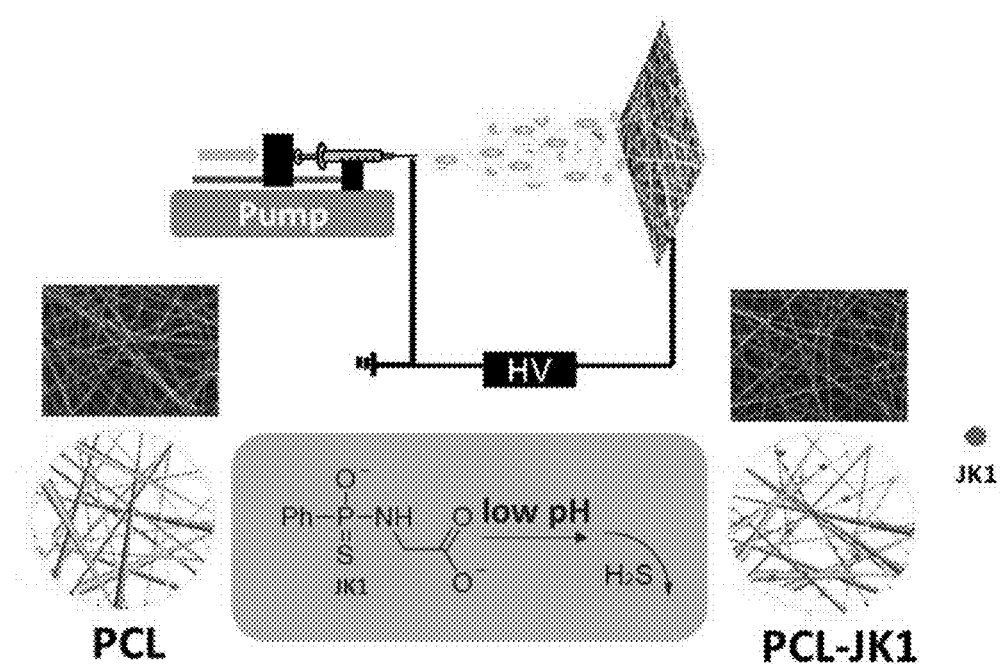
FIG. 3 illustrates a system use for forming a nanofiber scaffold containing JK-1 for use as a wound healing dressing.
Figure 4A:
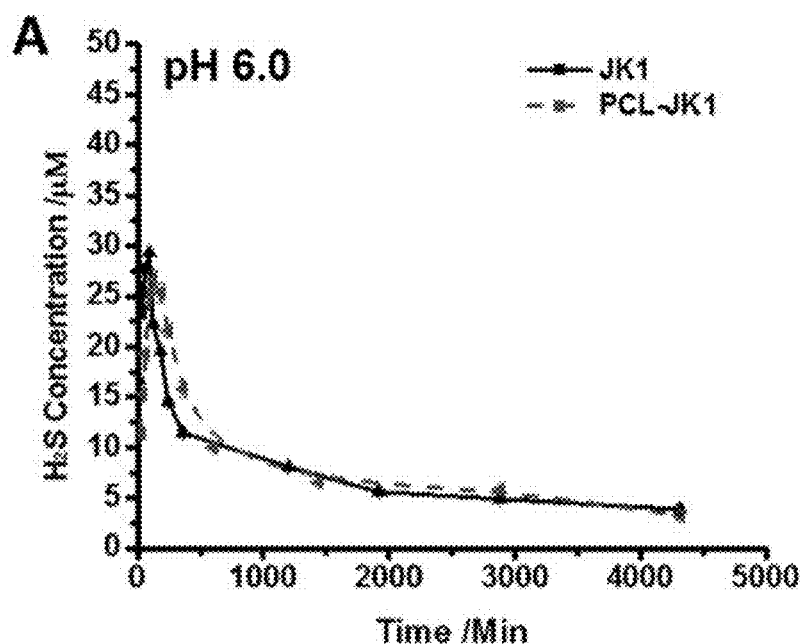
FIG. 4A is a graph showing the $H_2S$ release kinetics of donor JK-1 versus a PCL-JK-1 fiber with 10% JK-1 at a pH of 6.0 for a time frame of about 4500 minutes.
Figure 4B:
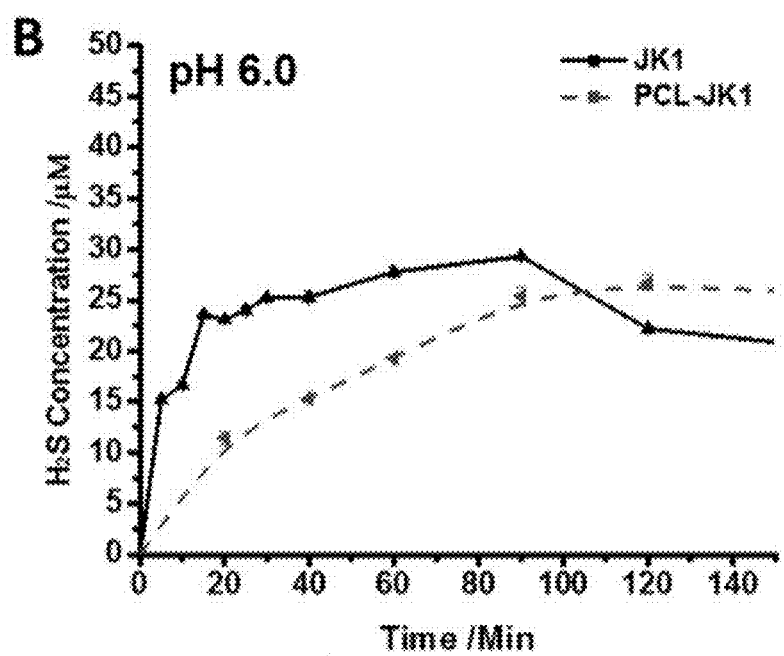
FIG. 4B is a graph showing the $H_2S$ release kinetics of donor JK-1 versus a PCL-JK-1 fiber with 10% JK-1 at a pH of 6.0 for a time frame of about 150 minutes.
Figure 4C:
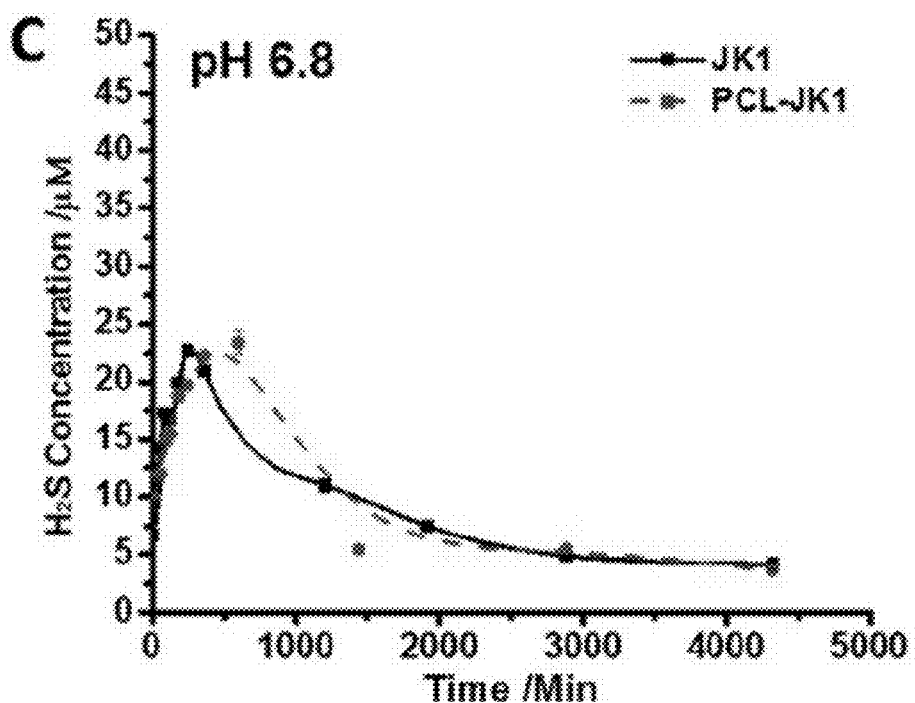
FIG. 4C is a graph showing the $H_2S$ release kinetics of donor JK-1 versus a PCL-JK-1 fiber with 10% JK-1 at a pH of 6.8 for a time frame of about 4500 minutes.
Figure 4D:
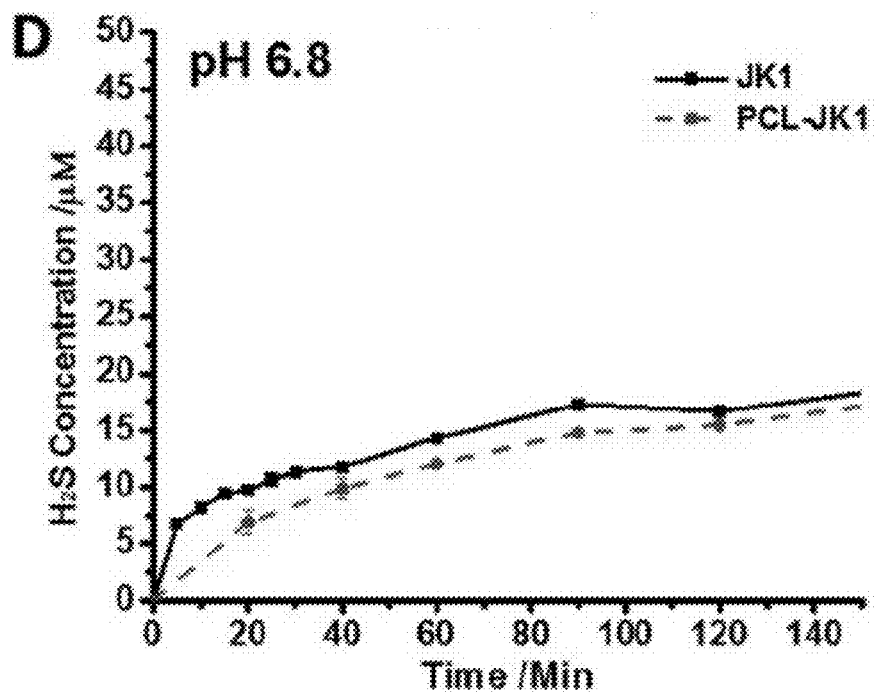
FIG. 4D is a graph showing the $H_2S$ release kinetics of donor JK-1 versus a PCL-JK-1 fiber with 10% JK-1 at a pH of 6.8 for a time frame of about 150 minutes.
Figure 4E:
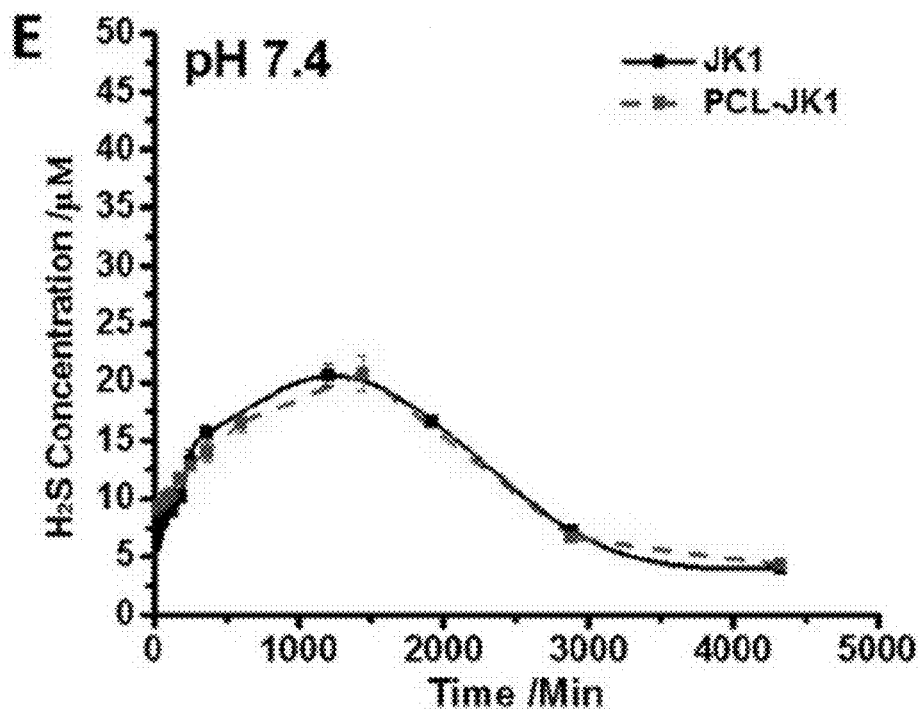
FIG. 4E is a graph showing the $H_2S$ release kinetics of donor JK-1 versus a PCL-JK-1 fiber with 10% JK-1 at a pH of 7.4 for a time frame of about 4500 minutes.
Figure 4F:
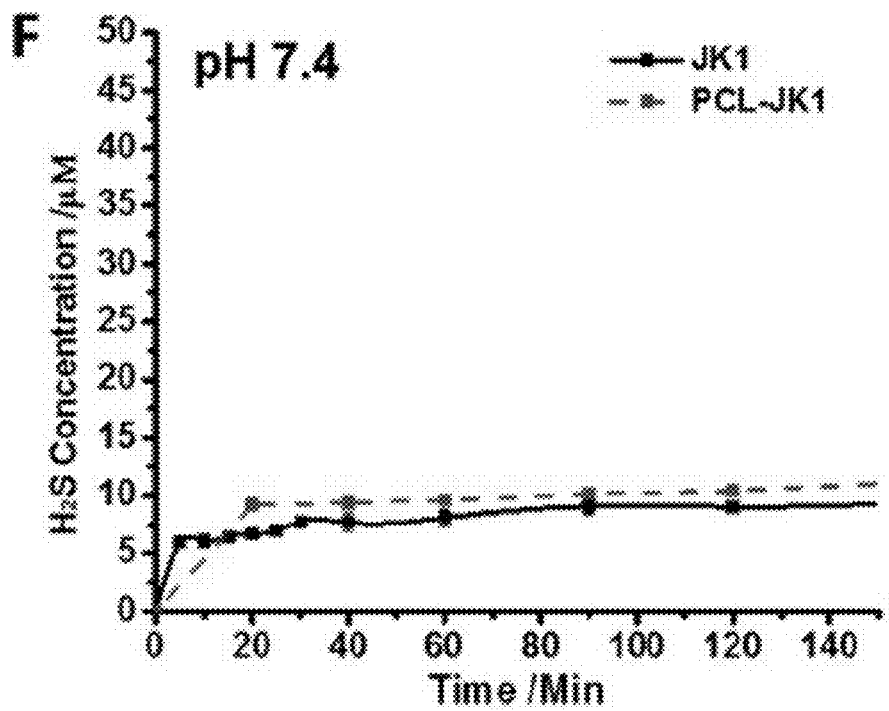
FIG. 4F is a graph showing the $H_2S$ release kinetics of donor JK-1 versus a PCL-JK-1 fiber with 10% JK-1 at a pH of 7.4 for a time frame of about 150 minutes.

In one particular embodiment, the nanofibrous scaffold can be formed from a biodegradable polymer such as polycaprolactone (PCL), polylactic acid (PLA), polyglycolic acid (PGA), or a combination thereof. Further, the nanofibrous scaffold can be formed from fibers having a fiber diameter ranging from about 50 nanometers (nm) to about 750 nm, such as from about 75 nm to about 650 nm, such as from about 100 nm to about 400 nm. Moreover, the nanofibrous scaffold can be an electropun nanofibrous scaffold. Electrospun nanofibrous scaffolds can be considered good candidates for drug delivery material dues to their high surface-to-volume ratio and porosity. Electrospinning is a technique that fabricates non-woven sheets of fibers as shown in FIG. 3. These sheets of fibers can closely resemble a bandage or wound dressing type of material, and are soft and easy to handle.

In another embodiment, the biodegradable scaffold material can be in the form of a sponge. The sponge can be formed from sodium alginate, which can be isolated from marine algae and well dissolved in water due to negatively charged carbonyl group. Alginate is widely used in industry and medicine for many applications such as scaffolds and wound dressings due to low toxicity, favorable mechanical properties, and capacity for bioresorption of the constituent materials. The high water absorption ability of alginate leads to absorb wound exudate and retain moist wound environment. Alginate can be processed into dressings with various shapes and sizes and widely used in the treatment of exuding wounds. Guluronate units in alginate enable the polymer to become hydrogel by crosslinking through divalent cations such as $Ca^{2+}$. A sodium alginate sponge/hydrogel is pH-sensitive and can have hemostatic properties. By incorporating the sodium alginate sponge/hydrogel wound dressing with the $H_2S$ donor JK-1, the resulting composite can absorb wound exudate to form a hydrogel and retain a moist wound environment. With the absorption of wound exudate and the subsequent decrease in pH, the dressing can then release $H_2S$ consistently, which can accelerate wound healing process by improving cell proliferation, migration, and angiogenesis.

In yet another embodiment, the biodegradable scaffold material can include a hyaluronic acid-based hydrogel. Hydrogels are able to donate moisture to dehydrated tissue and absorb some moisture from an exudating wound. Hydrogels are widely used as debriding agents in the management of a variety of wounds. Hydrogels also help to maintain a moist wound environment recognized as being beneficial in wound healing. Hyaluronic acid (hyaluronan, HA) is a naturally-occurring linear polysaccharide formed from disaccharide units containing N-acetyl-D-glucosamine and glucuronic acid. It forms a smaller part of the extracellular matrix (ECM) but has the significant advantage of structural conservation regardless of the source and is therefore nonallergenic. The degradation products of HA can modulate wound healing, allowing the use of HA in clinical applications as diverse as dermal scaffolds, cartilage defects, glial cell culture, and regeneration. The molecule is readily soluble in water, producing a gel that behaves as a lubricant as well as adsorbing water, lending it hygroscopic and homeostatic properties. In some embodiments, the HA can be modified such that the biodegradable scaffold material can include methacrylated hyaluronic acid having a degree of modification ranging from about 30% to about 60%, such as from about 35% to about 55%, such as from about 40% to about 50%. The use of methacrylated HA facilitates the formation of the HA into a hydrogel.

In an additional embodiment, the biodegradable scaffold material can be cross-linked so that it maintains its structure integrity when introduced into a moist environment, such as an area of skin around a wound. Although any suitable cross-linking agent can be utilized, in one embodiment, the cross-linking agent can include calcium chloride, while in another embodiment, the cross-linking agent can include dithiotreitol (DTT). The DTT can be present in an amount ranging from about 0.0001% (w/v) to about 0.002% (w/v). Other cross-linking agents that can be used include cross-linking agents with multi-thiol groups such as PEG-4SH (molecular weight 5000, pentaerythritol core), which can be present in an amount ranging from about 1% (w/v) to about 3% (w/v).

The present invention may be better understood with reference to the following examples.

EXAMPLE 1—ELECTROPSUN POLYCAPROLACTIONE

In Example 1, a composition and method to fabricate a JK-1-doped polycaprolactone (PCL) electrospun nanofiber dressing for promoting the wound healing process was investigated.

Materials and Methods $H_2S$ donor JK-1 was freshly prepared before electrospinning. Polycaprolactone (PCL) (Average Mn Ca. 60 kDa, Sigma) was dissolved in 1,1,1,3,3,3-hexafluoro-2-propanol (HFIP, Scientific Matrix) to afford a 6% w/w solution; then different amounts of JK-1 solution (200 mM) were added to prepare samples with $H_2S$ donors at various concentrations (0%, 1%, 5% and 10% to PCL, w/w). The random nanofibers were obtained by a home-made electrospinning system (see FIG. 3) through stationary collector described before with a flow rate at 3 μL/min, high voltage (HV) supply between 10-11 kV, and humidity below 1%.

The morphology of the PCL and PCL-donor fibrous scaffolds were examined by a scanning electron microscopy (SEM, VEGA3 TESCAN). Fiber samples were dried under nitrogen flow before being coated with gold with a Desk II cold sputter coater (Denton Vacuum, Morristown, N.J.) for 60 seconds. At least three areas were randomly selected to test the uniformity of the fibers. In addition, infrared spectrometry of the PCL and different PCL-JK-1 (1%, 5%, 10%) scaffolds were taken using a Spectrum 100 (FT-IR) Spectrometer.

Measurements of release kinetics of $H_2S$ from fibrous scaffold were conducted at each time point. For each experiment, 20 mg fibrous scaffold was immersed in 50 mL PBS under different pH (pH 7.4, pH 6.8 and pH 6.0). Reaction aliquots (0.5 mL) were added to mixture of zinc acetate (50 μL, 1% w/v in $H_2O$) and NaOH (6.25 μL, 1.5M) in 1.5 mL centrifuge tubes at certain time intervals. Then centrifuge at 20500 rcf for 1 hour, followed by removing the supernatant using a pipette. $FeCl_3$ (100 μL, 30 mM in 1.2 M HCl), and N,N-dimethyl-p-phenylenediamine sulfate (100 μL, 20 mM in 7.2 M HCl) was added to centrifuge tubes. At last, solutions are transferred to 96 microplate followed by addition of 1 mL water, and absorbance readings (670 nm) were taken after 20 minutes.

The mouse fibroblast cell line NIT 3T3 was purchased from American Type Culture collection. Cells were maintained in Dulbecco's Modified Eagle Medium (DMEM, #D6046, Sigma-Aldrich) supplemented with 10% heat inactivated fetal bovine serum (Hyclone, Thermo Scientific), 100 U/mL penicillin and 100 μg/mL streptomycin (Gibco BRL, Invitrogen Corp., Carlsbad, Calif., USA). Cells were cultured in a 5% $CO_2$ humidified incubator at 37° C. Sterilized PCL and PCL-donor JK-1 fibrous scaffolds were soaked in media for 30 min before cell seeding. Cells were then trypsinized and seeded on PCL or PCL-JK-1 scaffolds at a cell density of $5 \times 10^3$ cells per $cm^2$.

NIH 3T3 was trypsinized and washed by PBS (3×) and resuspended in 1 mL PBS supplemented with Cell Tracker™ deep red dye (2 μM). Cells were stained for 30 min at 37° C. and washed by PBS (3×) and resuspended in 2 mL DMEM culture medium (pH 7.4 and pH 6.0 adjusted by HCl). Cells were then counted and seeded in 6-well plate with PCL or PCL-JK-1 fibrous scaffold (10% w/w JK-1 to PCL) under pH 6.0 and pH 7.4, respectively. Cell density was 40,000 cells for individual well. All cells were incubated under a humidified atmosphere of 5% $CO_2$. At each time points (12 h, 24 h, 54 h, 72 h), cells were directly observed under the fluorescence microscopy (Olympus IX81, Olympus America Inc.).

Male C57BL/6 mice weighing 20 g were provided by the Laboratory Animals Center of Wenzhou Medical University, and treated strictly in accordance with international ethical guidelines and the National Institutes of Health Guide concerning the Care and Use of Laboratory Animals. The mouse was anesthetized with 4% chloral hydrate and the skin was cleaned with shaving machine and depilatory creams. Silicone rings with an internal diameter of 8 millimeters and a thickness of 0.5 millimeters were stitched on the skin. Two full-thickness wounds per mice were created on their mid-back with 6 mm diameter puncher (Acuderm® Inc., Ft Lauderdale, Fla., USA). Photographs were taken of each wound. PCL fiber and PCL-Donor (10% w/w JK-1 to PCL) with diameter of 7 mm were deposited in wound area. Wounds were covered with 3M Tegaderm Film (3M Health Care, Germany) and medical bandages. After surgery, photos were taken at days 7, 10, 14, 17, 20 and analyzed using Image-Pro plus. The ratio of wound healing was calculated using equation 1:

$$C(\%) = \frac{C_O - C_f}{C_O} \times 100\% \quad (1)$$

where C % is the wound healing closure ratio, $C_O$ is the original wound area, and $C_f$ is the open area on point day.

Skin histological analysis was performed on day 7 and 20 after surgery. Briefly, the wound area were picked after anesthesia and euthanized. The skin tissues were fixed in 4% paraformaldehyde at 4° C. overnight then embedded in paraffin, followed by cutting in 5 μm sections with a microtome (LEICA RM2235, Germany) and placed in a 65° C. oven 4 h.

For Hematoxylin and Eosin staining, tissue sections were put on xylene for 20 minutes, 100% alcohol for 5 minutes, 95% alcohol for 2 minutes, 80% alcohol for 2 minutes, distilled water for 5 minutes, then hematoxylin (Beyotime Institute of Biotechnology, China) stained nuclear for 5 minutes, followed by a PBS wash for 3 minutes to remove excess hematoxylin, and then eosin (Beyotime Institute of Biotechnology, China) staining of the extracellular matrix for 2 minutes. After that, the sections were washed with distilled water for 5 minutes, followed by 80% alcohol for 2 minutes, 95% alcohol for 2 minutes, 100% alcohol for 5 minutes, and xylene for 10 minutes, after which the sections were covered with neutral resin. Photographs were taken with Nikon microscope (Nikon, Tokyo, Japan).

For Masson's trichrome staining, tissue sections were stained using Masson's trichrome staining kit (Beyotime) including a hydration step, 5 minutes washing with distilled water, nuclear staining with A1:A2 (1:1) for 5 minutes, thoroughly rinsed with water and used acid alcohol differentiation 3 seconds, then Ponceau acid fuchsin solution stained fibrous tissue 5 minutes, 2% acetic acid solution soak for 1 minute, and differentiation with phosphomolybdic acid solution for 1 minutes, followed by direct use of aniline blue staining for 80 seconds without washing, after which the sections were mounted, dehydrated by 80% alcohol for 3 seconds, 95% alcohol for 1 minute, 100% alcohol for 5 minutes, and xylene for 10 minutes. The sections of tissue were then covered with neutral resin. Photographs were taken with Nikon microscope (Nikon, Tokyo, Japan).

For immune-histochemical staining of cytokeratin, after dewaxing and hydration of the tissue sections, 3% hydrogen peroxide (15 minutes) was used to block the endogenous peroxidase. Primary antibodies for cytokeratin (ab9377, Abcam) were diluted in phosphate-buffered saline (1:200) containing 1% bovine serum albumin (BSA) overnight at 4° C. Biotinylated secondary antibodies were diluted with phosphate-buffered saline (1:1000) and incubated for 60 minutes in 37° C. DAB kit (ZSGB-BIO, Beijing, China) was used for 8 seconds to 3 minutes for all samples.

Results and Discussion

Figure 2:
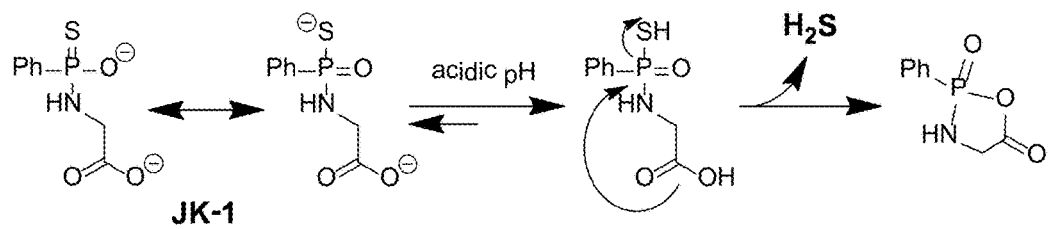
FIG. 2 is a schematic diagram illustrating the release of $H_2S$ from donor JK-1.

In Example 1, the PCL and PCL-JK-1 fibrous scaffolds were fabricated through an electrospinning approach as shown FIG. 3. The structure of JK-1 and the activated $H_2S$-releasing mechanism are shown in FIGS. 1 and 2, respectively, and this novel pH responsive $H_2S$ donor JK-1 was incorporated into a PCL solution before the electrospinning process was initiated. The mixed JK-1/PCL solution generated homogeneous nanofibers with smooth and uniform morphology and a diameter around 300 nanometers (nm), which is similar as the fibers generated from pure PCL solution. In addition, the FTIR spectrum was used to further confirm the successful loading of JK-1 into PCL-JK-1 fibrous scaffold. Specifically, the PCL fiber showed peaks at 2950, 2850 and 1720 $cm^{-1}$ due to the stretching vibration of —C═O bonds, while the PCL-JK-1 afforded additional peaks at 3320, 1607 and 720 $cm^{-1}$, which can be attributed to amide N—H stretch, amide N—H bending and aromatic C—H bending from JK-1, respectively. These data confirmed the JK-1 donor was incorporated into the nanofibers successfully.

Since $H_2S$ has now been recognized as a potent cytoprotective gasotransmitter, fabrication of bio-compatible scaffolds which can release $H_2S$ in a controlled manner could be a promising therapeutic strategy in biomedical applications. To determine the controlled $H_2S$ release profile from a PCL-JK-1 fibrous scaffold (with 10% JK-1) under different pHs (i.e. pH 6.0, 6.8 and 7.4), a modified Methylene Blue method was performed with JK-1 in solution as the control. As shown in FIGS. 4A, 4B, 4C, 4D, 4E, and 4F, similar to JK-1 alone, PCL-JK-1 exhibited a pH-dependent $H_2S$-releasing profile where a lower pH led to higher and faster release of $H_2S$ with and earlier peaking time (pH 6.0<pH 6.8<pH 7.4), as well as a higher $H_2S$ peak concentration (pH 6.0>pH 6.8>pH 7.4). However, notable slower $H_2S$ release was observed for PCL-JK-1 nanofibers, especially at the early stage in the process. For instance, under pH 6.0 (FIG. 4B), PCL-JK-1 did not produce a peak in $H_2S$ within 120 min. In contrast, JK-1 immediately reached peak concentration within 10 minutes, suggesting extended $H_2S$ releasing profiles from PCL-JK-1 nanofibrous scaffolds compared with the JK-1 $H_2S$ donor only. These results indicate that PCL-JK-1 nanofibrous scaffolds could release $H_2S$ in response to the pH of the environment and prolong the $H_2S$ release from the JK-1 donor component.

Figure 5A:
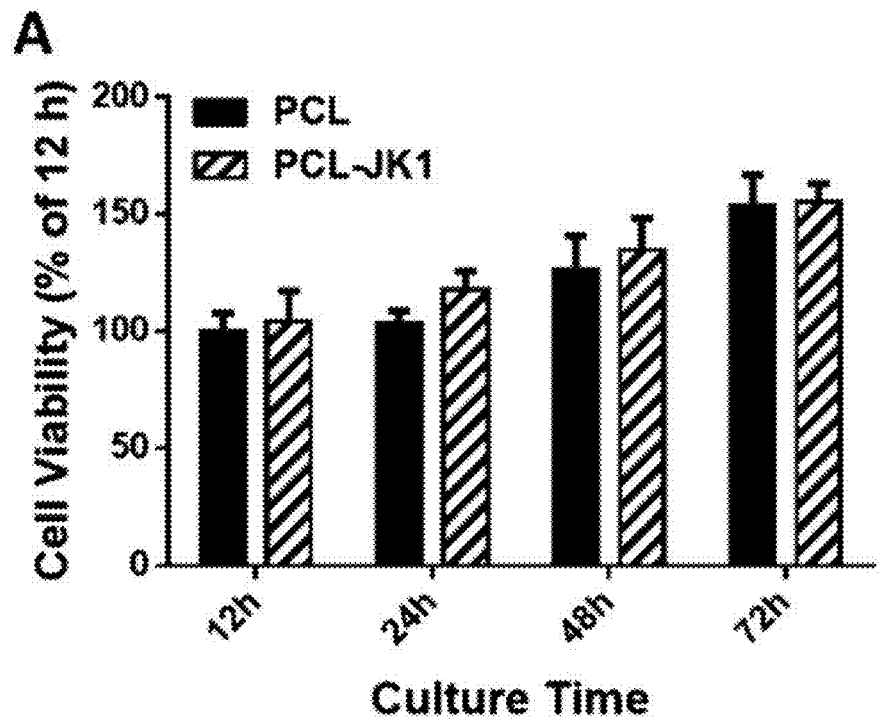
FIG. 5A is a graph comparing the cell viability versus time of cells cultured on PCL fibers with cells cultured on PCL-JK-1 fibers at a pH of 7.4.
Figure 5B:
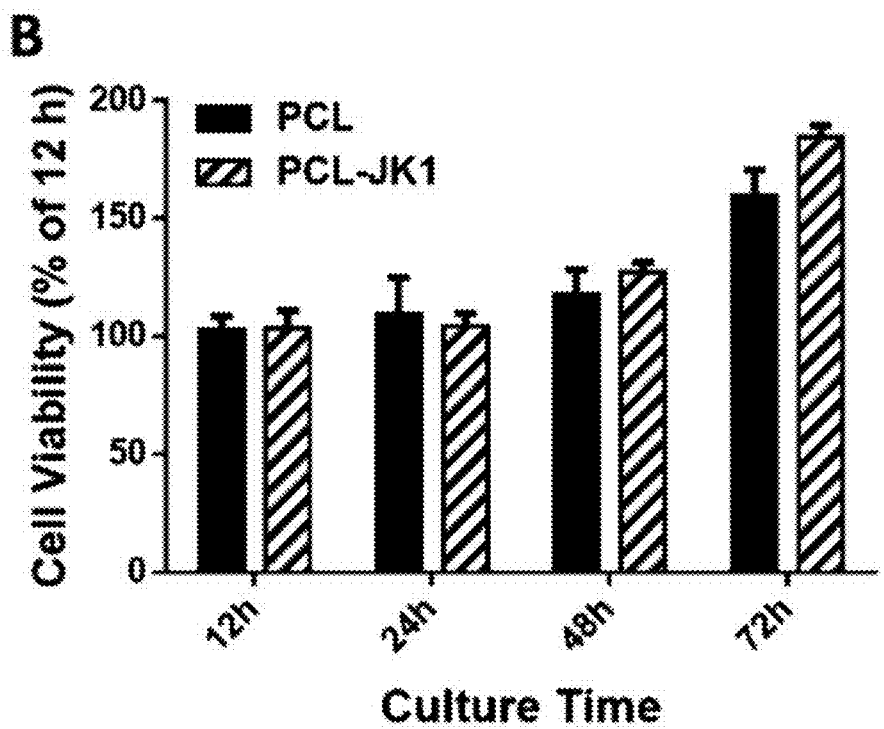
FIG. 5B is a graph comparing the cell viability versus time of cells cultured on PCL fibers with cells cultured on PCL-JK-1 fibers at a pH of 6.8.

Before the PCL-JK-1 scaffolds were applied to the in vivo wound model, in vitro investigation of their cyto-compatibility versus PCL scaffolds alone were carried out using NIH 3T3 fibroblast cells because fibroblasts play an important role in wound regeneration process. Since pH value could affect JK-1's $H_2S$ release behavior, both pH 7.4 and pH 6.0 were chosen to compare the toxicity of PCL-JK-1 scaffolds upon culturing for 12 hours, 24 hours, 48 hours, and 72 hours versus PCL scaffolds. We observed no difference in cell viability between PCL and PCL-JK-1 at both pH 6.0 (see FIG. 5A) and pH 7.4 (see FIG. 5B) upon culturing for 72 hours. This data demonstrated that JK-1 doped PCL fibers were non-toxic to fibroblast cells, which is essential for the wound healing process. Therefore, we assumed that PCL-JK-1 was able to maintain its capacity to support fibroblast cell proliferation in vivo.

In vivo experiments were then carried out to evaluate the actual wound healing efficacy of the $H_2S$ releasing PCL nanofibrous scaffold of the present invention. It was reported that $H_2S$ is a potential gasotransmitter upon wound regeneration because it could promote endothelial cell migration, micro vessel tube formation as well as angiogenesis through vascular endothelial growth factor receptor 2 (VEGF-2) pathway. Serious damage of skin integrity would cause severe inflammation, losing skin appendages such as vascular and hair follicles, and following by prolonged healing process. Thus in this work, full-thickness removal skin resulting in cutaneous wounds in C57BL/6 mice were created to study the wound healing capability of $H_2S$ releasing fibers.

Figure 6A:
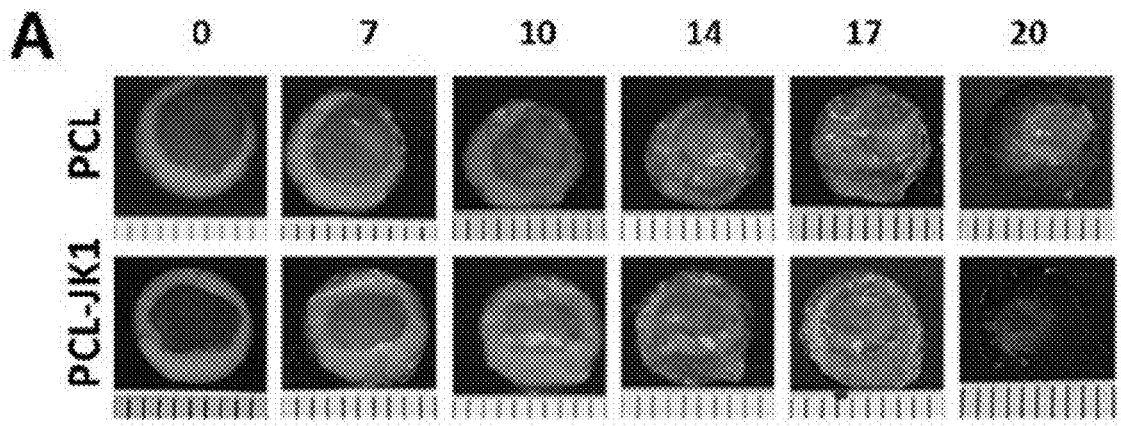
FIG. 6A is a series of images showing the level of wound closure upon treatment with a PCL fibrous scaffold and a PCL-JK-1 fibrous scaffold for a time period from 0 days to 20 days.
Figure 6B:
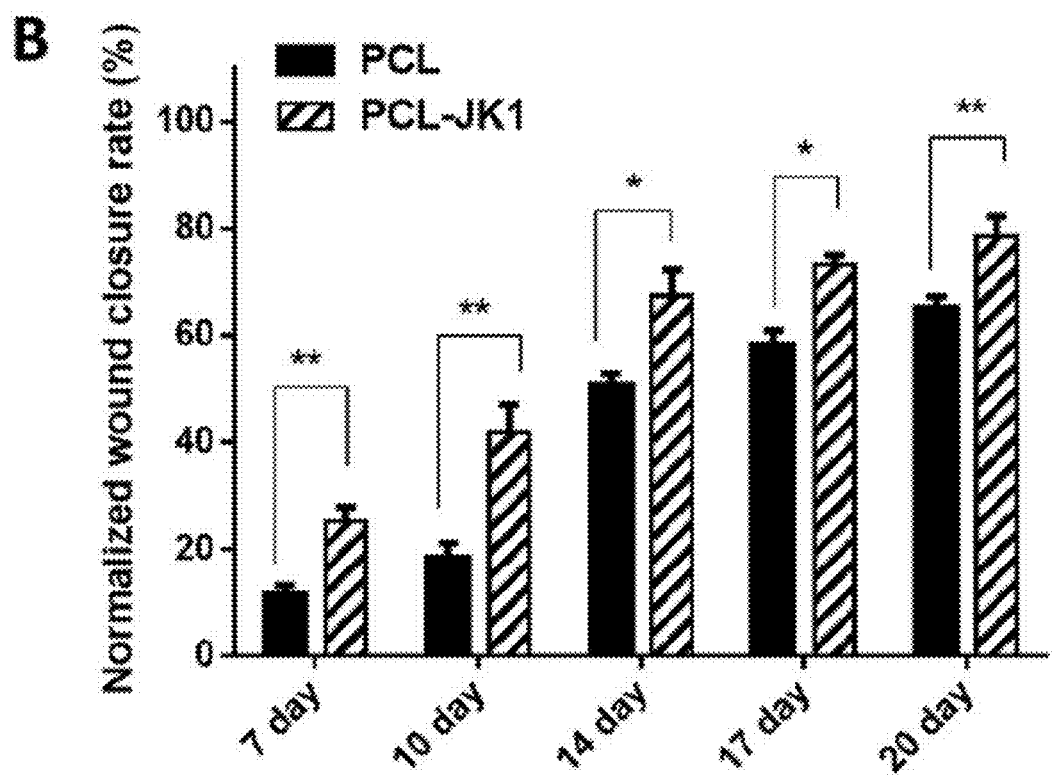
FIG. 6B is a graph comparing the wound closure rates for wounds treated with PCL fibrous scaffolds and PCL-JK-1 fibrous scaffolds.

The wound healing progress was analyzed at different time points during 20 days upon treatment. FIG. 6A shows the sequential macroscopic images of full-thickness models treated with PCL and PCL-JK-1 scaffolds (with 10% JK-1) for 0, 7, 10, 14, 17 and 20 days. It can be seen that wounds were gradually regenerated from the edge of wound. Compared to PCL treated wounds, PCL-JK-1 treated wounds enhanced wound closure at each time point, suggesting the positive function of the PCL-JK-1 dressing likely due to the $H_2S$ releasing. Quantitatively, FIG. 6B calculated the wound closure rates for both PCL and PCL-JK-1 treated wounds. Consistent with visual macroscopic images of wound in FIG. 6A, the healing rate of PCL-JK-1 treated group was significantly higher than that of PCL at all time points studied (days 7, 10, 14 and 17). Especially at day 20, the final closure rate for PCL-JK-1 treated group was 15% higher than that of the PCL treated wounds, with a wound closure rate of 78.7±8.8% in contrast to 64.8±6.8% for the PCL scaffold alone. Both the macroscopic observation and quantified wound closure rate data reveal that the healing of the wound is significantly improved by treatment with $H_2S$ releasing fibers of PCL-JK-1 compared to PCL fibers alone.

Figure 7A:
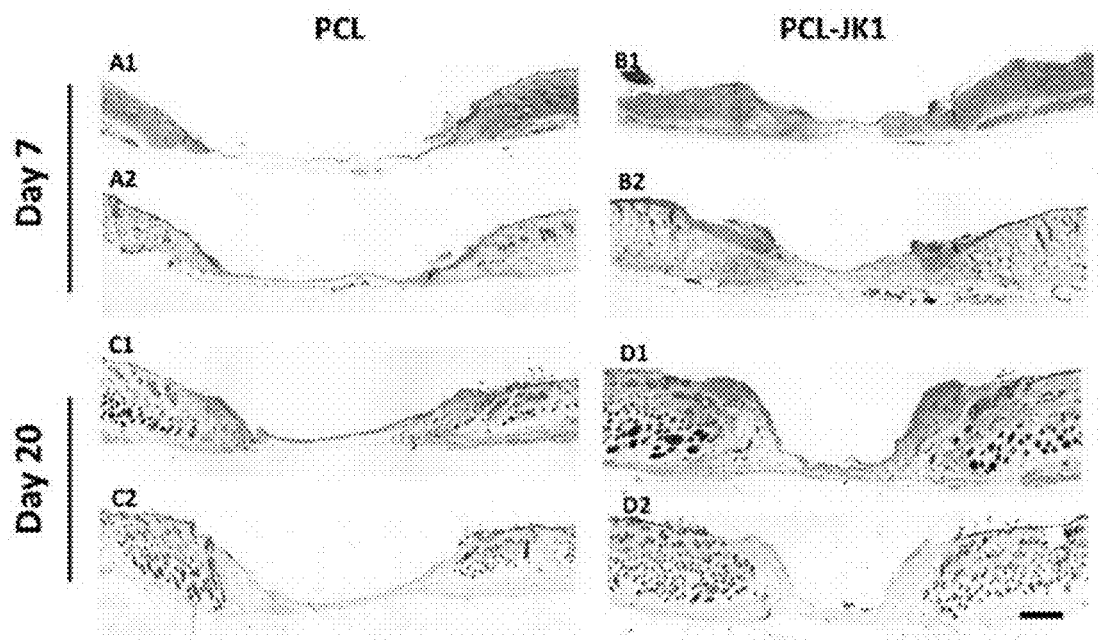
FIG. 7A is a series of histological images of a wound site at day 7 and day 20 for a wound treated with a PCL fibrous scaffold and a wound treated with a PCL-JK-1 fibrous scaffold, where images A1, B1, C1, and D1 are tissue sections stained with Hematoxylin and Eosin and images A2, B2, C2 and D2 are tissue sections stained with cytokeratin.
Figure 7B:
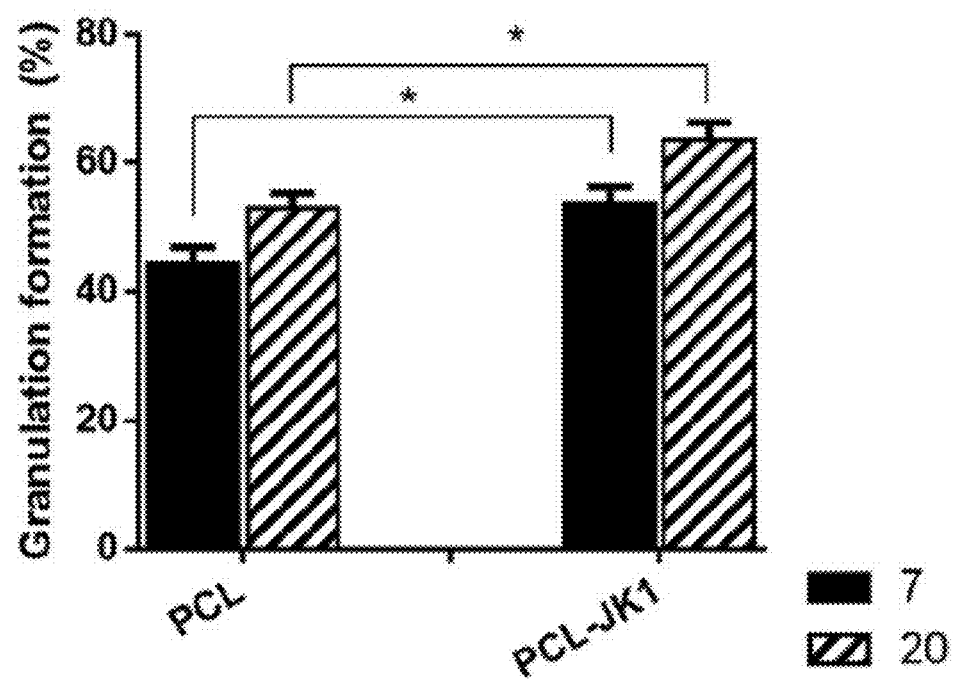
FIG. 7B is a graph comparing the granulation formation (%) calculated from Hematoxylin and Eosin staining for a wound treated with a PCL scaffold (day 7 and 20) with a wound treated with a PCL-JK-1 scaffold (day 7 and 20).
Figure 7C:
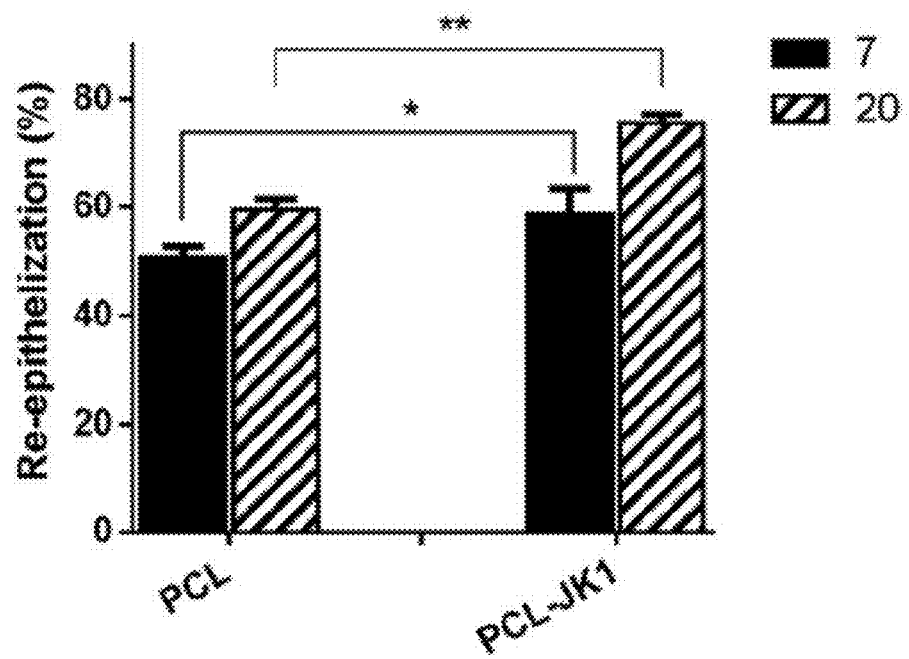
FIG. 7C is a graph comparing the re-epithelization (%) calculated from cytokeratin staining for a wound treated with a PCL scaffold (day 7 and 20) with a wound treated with a PCL-JK-1 scaffold (day 7 and 20).

Wound regeneration comprises granulation tissue formation and re-epithelialization. Representative H&E-stained histological formed granulation tissue images and immunohistochemical staining of cytokeratin images used to evaluate the wound healing progress are shown in FIG. 7A. On day 7, PCL group showed a very thin granulation tissue layer (image A1), a translucent lighter cytokeratin positive cells (image A2), and a large length of unhealed wound remaining. Meanwhile, for the PCL-JK-1 treated group, thicker tissue formation (image B1) and deeper cytokeratin positive cells (image B2) appeared in the injured wound area with a relatively smaller length of unhealed wound remaining, implying that PCL-JK-1 promoted faster wound healing than PCL scaffolds corresponding to migration phase of healing process. On day 20, the PCL treated wound still had a larger wound area with thin granulation formation (image C1) and insufficient developed epithelialization (image C2). On the other hand, for the PCL-JK-1 treated group, the newly regenerated dermis and the formed tissues are connected tightly (image D1) and filled with sufficient appendants such as hair follicles under fully healed epithelialization layer (image D2). In addition, the newly regenerated tissues was very similar to normal skin with fully developed granulation and re-epithelialization. This further indicates that the PCL-JK-1 matrix of the present invention is able to facilitate faster and more efficient wound regeneration than PCL fibers towards full-thickness wounds. Furthermore, the granulation formation (FIG. 7B) and re-epithelization (FIG. 7C) for PCL and PCL-JK-1 were quantitatively analyzed on day 7 and day 20. Again, PCL-JK-1 exhibited significantly accelerating healing effects compared with PCL alone due to the release of $H_2S$ from the PCL-JK-1 nanofibers.

Figure 8A:
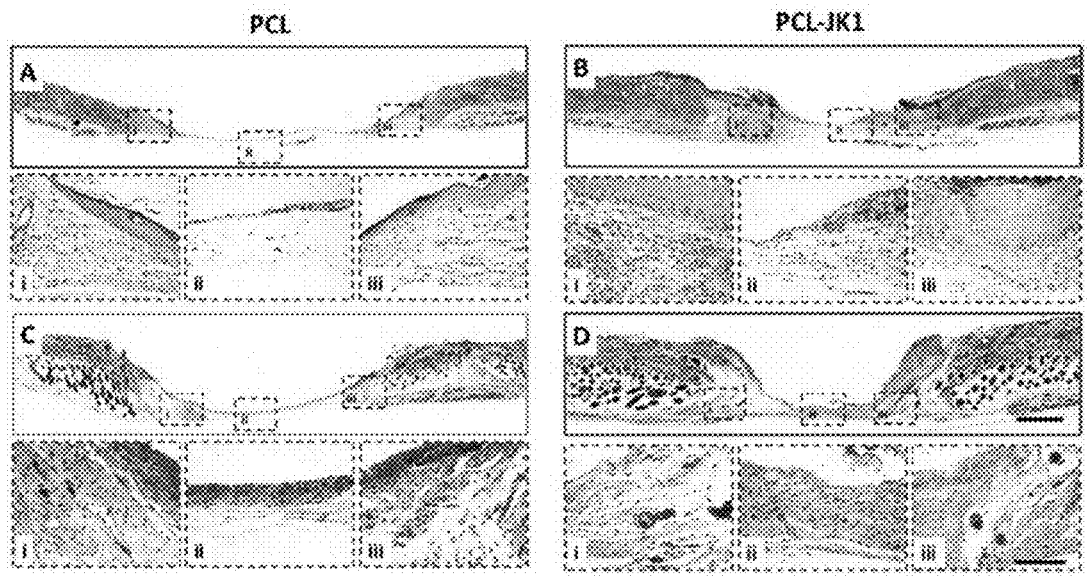
FIG. 8A is a series of histological images of a wound site at day 7 and day for a wound treated with a PCL fibrous scaffold and a wound treated with a PCL-JK-1 fibrous scaffold after Masson trichrome staining to show collagen deposition, where the magnified images of squares I, ii, and ii in images A-D are shown under each image, where images A and B represent the wound sites on day 7 and images C and D represent the wound sites on day 20.
Figure 8B:
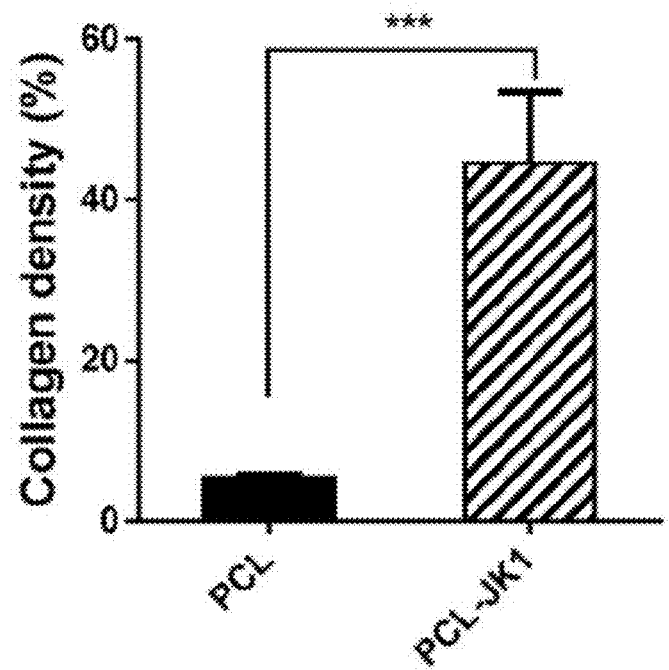
FIG. 8B is a graph showing the collagen density (%) on day 7 for the PCL scaffold and the PCL-JK-1 scaffold.
Figure 8C:
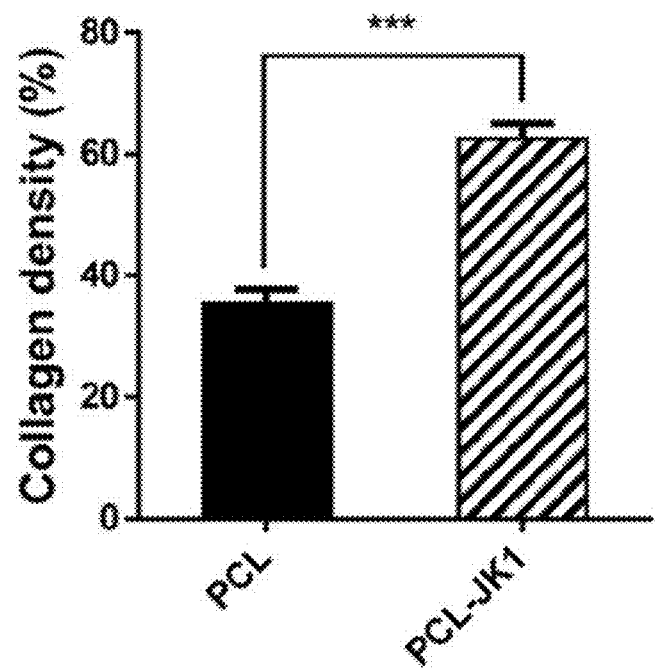
FIG. 8C is a graph showing the collagen density (%) on day 20 for the PCL scaffold and the PCL-JK-1 scaffold.

Masson's trichrome staining with collagen elements in blue, cellular components keratin and muscle fibers in pink, revealed much clearer matricial collagen deposition upon wound regeneration. FIG. 8A depicts the collagen deposition in regenerated skin for specific time intervals. On day 7, little collagen fibers were shown in the PCL treated group (image A) either on the edge of wound (magnified i and ii under the post-wound image) nor the wound bed (magnified ii under the post-wound image). However, for the PCL-JK-1 treated group (image B), much higher collagen deposition was revealed compared to the PCL treated group, and some collagen bundles are beginning to appear especially at the wound edge (magnified images of i and iii). On day 20, a larger number of collagen bundles and more regular deposition of thicker collagen was presented by the PCL-JK-1 treated group (image D and its images i, ii, and iii) compared to the PCL group (image C and its images i, ii, and iii), further indicating the enhanced wound healing capability of PCL-JK-1 fibrous scaffold. In addition, quantified evaluation of collagen deposition upon post wound on day 7 and day 20 are shown in FIG. 8B and FIG. 8C, respectively. As shown, deposition of collagen for the PCL-JK-1 treated scaffold is significantly higher than the PCL scaffold on both day 7 (44.5±19.8% versus 5.5±0.6%) and day 20 (62.5±5.6% versus 35.5±5.1%), indicating obvious enhanced neo-tissue formation by incorporating JK-1 into the PCL scaffold.

Considering the above results, compared to a PCL scaffold, a PCL-JK-1 scaffold was demonstrated to exhibit significantly improved wound recovery efficiency on granulation tissue formation along with wound re-epithelialization and collagen deposition, as well as neovascularization toward wound due to its release of $H_2S$.

The PCL fibrous matrix that doped the pH-controllable $H_2S$ releasing donor JK-1 was used as a wound healing scaffold to accelerate wound regeneration by releasing $H_2S$. The obtained PCL-JK-1 hybrid nanofibers showed pH regulated $H_2S$ releasing behavior as well as comparatively slower releasing rate by contrast to JK-1 in solution, and excellent cyto-compatibility in vitro. Further in vivo study showed that this hybrid PCL-JK-1 dressing exhibited obvious promoted dermal regeneration compared with PCL fibers being applied into the full-thickness removal wound healing model of C57BL/6 mice. Our data demonstrated that PCL-JK-1, as a $H_2S$ donor doped matrix, could indeed promote wound healing efficiency through H$_2$S's unique cyto-protective characteristics in vivo, likely due to special biological effects of H$_2$S such as inhibiting inflammation, reducing oxidative damage and increasing angiogenesis. At the moment, it is still hard to pinpoint how the pH-dependent release of H$_2$S contribute to different stages of the wound healing process. More systematic studies are undergoing to address this important issue in our group. Finally, as many of the effects of GYY4137 (a similar phosphine-sulfide based donor compound) are now being attributed to the phosphine-oxide side product, more control studies will be performed to confirm the physiological rule of H2S with careful designed in vivo experiments.

EXAMPLE 2—SODIUM ALGINATE SPONGE

In Example 2, a composition and method to fabricate a JK-1-doped sodium alginate (SA) sponge dressing for promoting the wound healing process was investigated.

Figure 9:
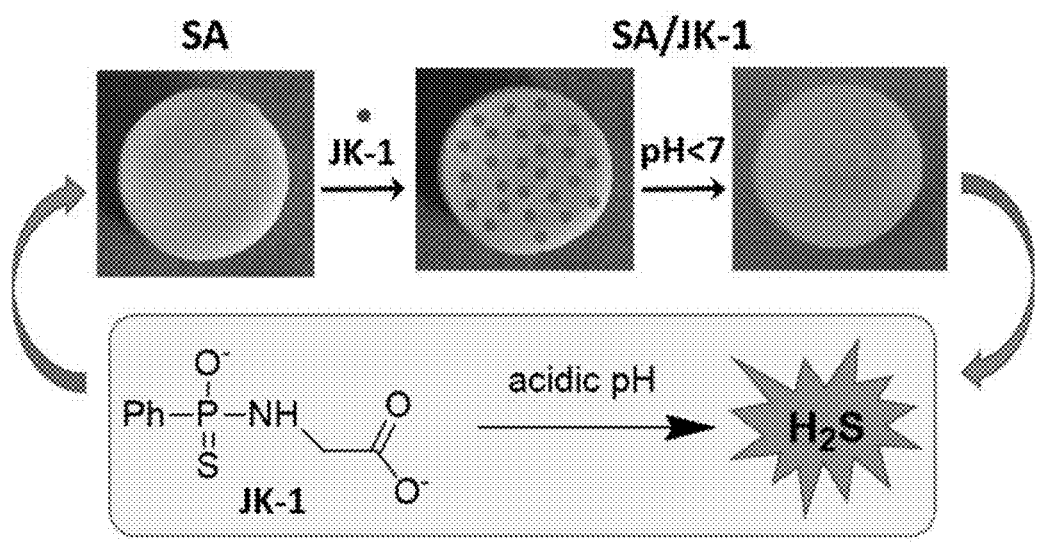
FIG. 9 is a schematic illustrating the fabrication of a sodium alginate sponge containing JK-1 for use as a wound healing dressing.

Aqueous sodium alginate (SA) solution was prepared at the concentrations of 1.0%, 1.5% and 2.0% (w/v). The SA solution was poured into the appropriate molds, then the trapped air bubbles were removed by storing at 4° C. for 1 hour. The molds were frozen overnight at −80° C., then lyophilized. The resulting sponges were treated with a calcium chloride (CaCl$_2$) solution at different concentrations (0.2 mM, 0.5 mM, and 1.0 mM) for 20 minutes to crosslink the SA sponge, then the sponges were frozen and lyophilized again. JK-1 was accurately weighed and dissolved in DI H$_2$O with the final concentration of 50 mM. The JK-1 solution was absorbed into the crosslinked SA sponge, then the sponges were again frozen and lyophilized as described above. The resulting samples were JK-1 loaded SA sponges (SA/JK-1) and the release of H$_2$S by varying the pH of the sponges was determined according to the schematic shown in FIG. 9.

Like the PCL nanofibrous dressings of Example 1, the SA/JK-1 sponges showed a pH-dependent H$_2$S releasing profile similar to that of JK-1, where a lower pH led to higher and faster release of H$_2$S (pH 5.0>pH 6.0>pH 7.4>pH 8.0), as well as higher H$_2$S peak concentration (pH 5.0>pH 6.0>pH 7.4>pH 8.0). It was noted that slower H$_2$S release was observed for the SA/JK-1 sponge at the early stage during the process under pH 6.0. Specifically, JK-1 reached H$_2$S peak concentration within 55 minutes, however, the SA/JK-1 sponge did not reach a peak even within 90 minutes, suggesting that SA sponge extended the H$_2$S releasing profiles of the JK-1 H$_2$S donor. These results indicate that the SA/JK-1 sponge could release H$_2$S in response to a controlled pH value and prolong the H$_2$S release by the JK-1 donor component. Since the pH value of a wound site is acidic, the pH-responsive SA/JK-1 dressing can release H$_2$S specifically with the absorption of the wound exudate, as well as provide a moist wound environment.

Figure 10:
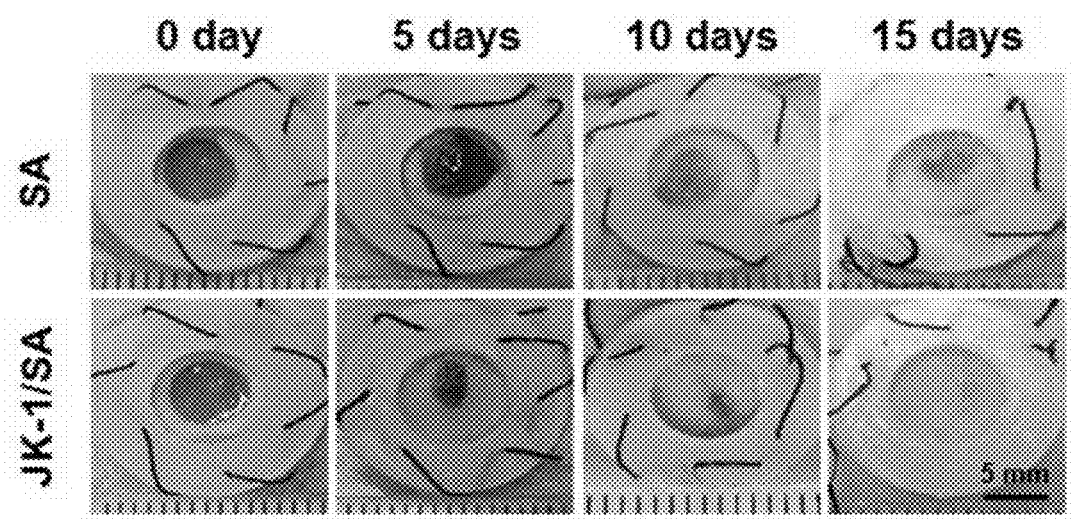
FIG. 10 is a series of images showing the level of wound closure upon treatment with sodium alginate and sodium alginate-JK-1 sponges for a time period from 0 days to 15 days.

In addition, in vitro cell culture indicated that the H$_2$S released by the SA/JK-1 sponges of the present invention at pH 6 could accelerate L929 fibroblast migration and repair scratch damage. Moreover, the JK-1 incorporated SA sponge was nontoxic to fibroblast cells, which is essential for the wound healing process. Further, the wound healing efficacy of the H$_2$S releasing SA sponge was studied on full-thickness removal of skin caused cutaneous wounds in ICR male mice at different time points during 15 days of treatment, as shown in FIG. 10. Compared with SA sponge treated wounds, the SA/JK-1 sponge treated wounds enhanced wound closure at each time point. Especially at day 15, the final closure rate for the SA/JK-1 treated group was about 32% higher than that of the SA treated wounds, with a wound closure rate of 89.5±6.7% in contrast to 57.3±5.3%. The data demonstrated that the healing of the wound was significantly improved by treatment with the H$_2$S releasing SA/JK-1 sponge.

On day 5, the SA sponge treated wound showed very short granulation tissue, translucent less cytokeratin positive cells, and little collagen fibers and there was a large length of unhealed wound left. Meanwhile, for the wound treated with the SA/JK-1 sponge, longer granulation tissue formation, more cytokeratin positive cells, and higher collagen expression was observed in the injured area with a comparatively smaller length of unhealed wound, which corresponds to the migration phase of healing process, implying that treatment of the wound with the SA/JK-1 sponge facilitated more efficient wound healing than the SA sponge without the JK-1. On day 15, the wound treated with the SA sponge corresponded with a larger wound area with short granulation formation and insufficient developed epithelialization. On the other hand, for the wound treated with the SA/JK-1 sponge, the newly regenerated dermis and the formed tissues were connected tightly as well as filled with sufficient appendant such as hair follicles under developed epithelialization. Moreover, large numbers of collagen bundles and more regular deposition of thicker collagen was present for the wound treated with the SA/JK-1 sponged compared to the wound treated with only the SA sponge. Further, the newly regenerated tissues formed in the wound treated with the SA/JK-1 sponge were very similar to normal skin with fully developed granulation and re-epithelialization. It is thus indicated that SA/JK-1 sponge is able to facilitate more rapid and efficient wound regeneration than SA sponge alone when used to treat full-thickness wounds. In summary, the SA/JK-1 sponge exhibited an improved healing effect as shown by re-epithelialization, granulation tissue formation, and collagen deposition, due to the releasing of H$_2$S by the JK-1 donor from the SA sponge based on the lower pH at the wound site.

EXAMPLE 3—HYALURONIC ACID HYDROGEL

In Example 3, a composition and method to fabricate a JK-1-doped hyaluronic acid (HA) hydrogel dressing for promoting the wound healing process is investigated.

Figure 11A:
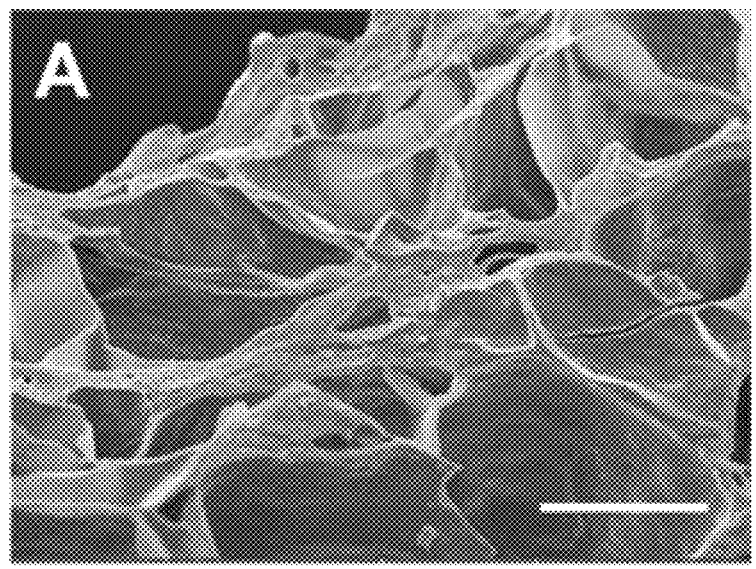
FIG. 11A is a scanning electron microscopy (SEM) image of a hyaluronic acid hydrogel.
Figure 11B:
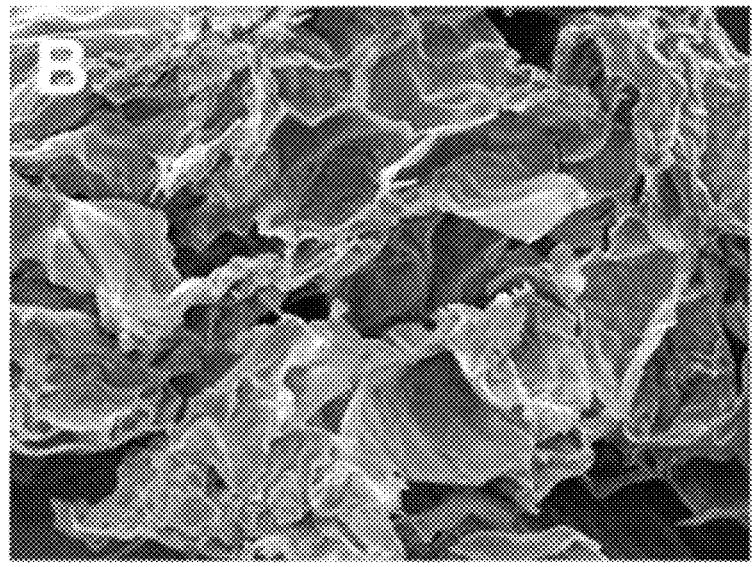
FIG. 11B is an SEM image of a hyaluronic acid-JK-1 hydrogel before $H_2S$ release.
Figure 11C:
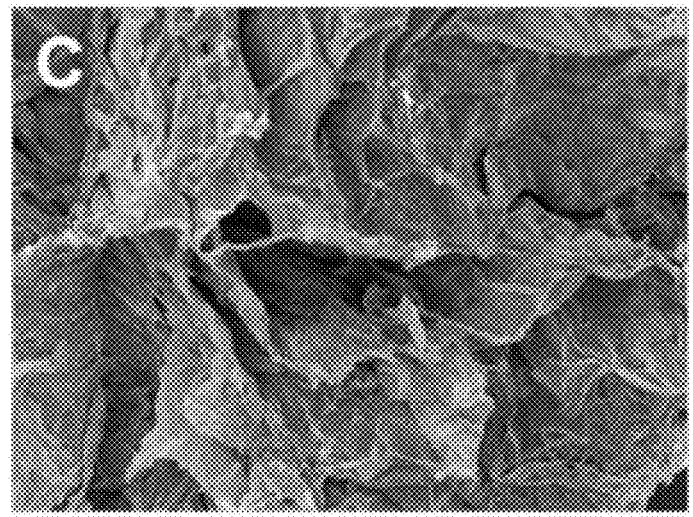
FIG. 11C is an SEM image of a hyaluronic acid-JK-1 hydrogel after $H_2S$ release.

HA having a molecular weight 47 kDa was dissolved at 1 wt. % in potassium phosphate buffer, pH 8, and methacrylic anhydride of different folds molar excess (relative to the HA disaccharide repeat unit), was added dropwise to the solution at 0° C. The pH of the two-phase reaction mixture was adjusted to 8.0 with 5 M NaOH aq., and the reaction continued for 24 hours at 4° C. with frequent re-adjustment of the solution pH. The product was dialyzed against milli-Q water for at least 48 hours, followed by centrifugation to remove the precipitate, which was then flash frozen in liquid nitrogen, and lyophilized, resulting in methacrylated hyaluronic acid (MeHA) that was analyzed by degree of modification by $^1$H NMR. To form the JK-1-doped HA hydrogels (HA/JK-1), MeHA polymers with 40%-50% degree of modification were dissolved in a phosphate buffer saline solution (PBS) at 5 wt. % concentration, and JK-1 in water was added to make a final concentration of 0.1 wt. %. A cross-linking agent, dithiotreitol (DTT), was then added at a molar ratio of thiol/ene=1:4. For comparison purposes, the HA hydrogels were also synthesized by the same procedure, except adding the JK-1 solution. FIG. 11A is a scanning electron micrograph (SEM) image of an HA hydrogel, while FIG. 11B is an SEM image of an HA hydrogel loaded with JK-1. Meanwhile, FIG. 11C is an SEM image of an HA-JK-1 hydrogel after the release of H₂S.

Figure 11D:
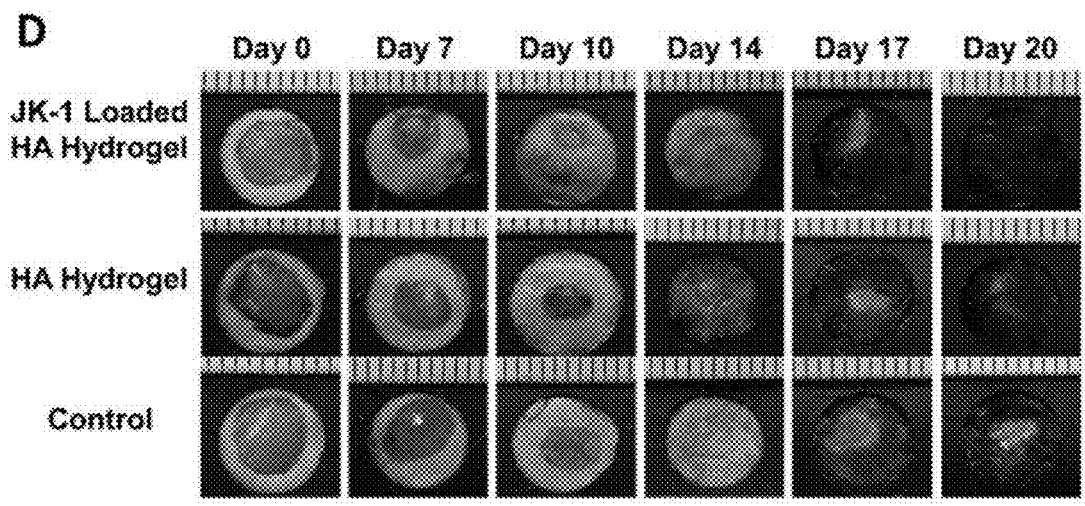
FIG. 11D is series of images showing the level of wound closure upon treatment with a hyaluronic acid hydrogel, a hyaluronic acid-JK-1 hydrogel, and a control for a time period from 0 days to 20 days.

The HA/JK-1 hydrogel dressing was applied at full-thickness in C57BL/6 mice to study the wound healing capability of the H₂S releasing hydrogel. Referring to FIG. 11D, compared with wounds treated with just an HA hydrogel, the wounds treated with the HA/JK-1 hydrogels showed enhanced wound closure at each time point (Day 7, Day 10, Day 14, Day 17, and Day 20, suggesting the positive function of the HA/JK-1 dressing likely due to the H₂S release. Both the macroscopic observation and quantified wound closure rate revealed that the healing of the wound was significantly improved by treatment with the H₂S releasing hydrogel containing HA/JK-1 compared to the HA-only hydrogel. On day 7, the HA hydrogel group showed a very thin granulation tissue layer, a translucent layer of lighter cytokeratin positive cells, and few collagen fibers. Meanwhile, for the HA/JK-1 hydrogel treated wound, thicker tissue formation, deeper cytokeratin positive cells, and much higher collagen deposition appeared in the injured wound area. On day 20, the HA/JK-1 hydrogel treated wound showed newly regenerated dermis and the formed tissues were connected tightly and filled with sufficient appendants such as hair follicles under a fully healed epithelialization layer, while HA treated wounds still had unclosed wound areas with thin granulation formation and insufficiently developed epithelialization.

Figure 12A:
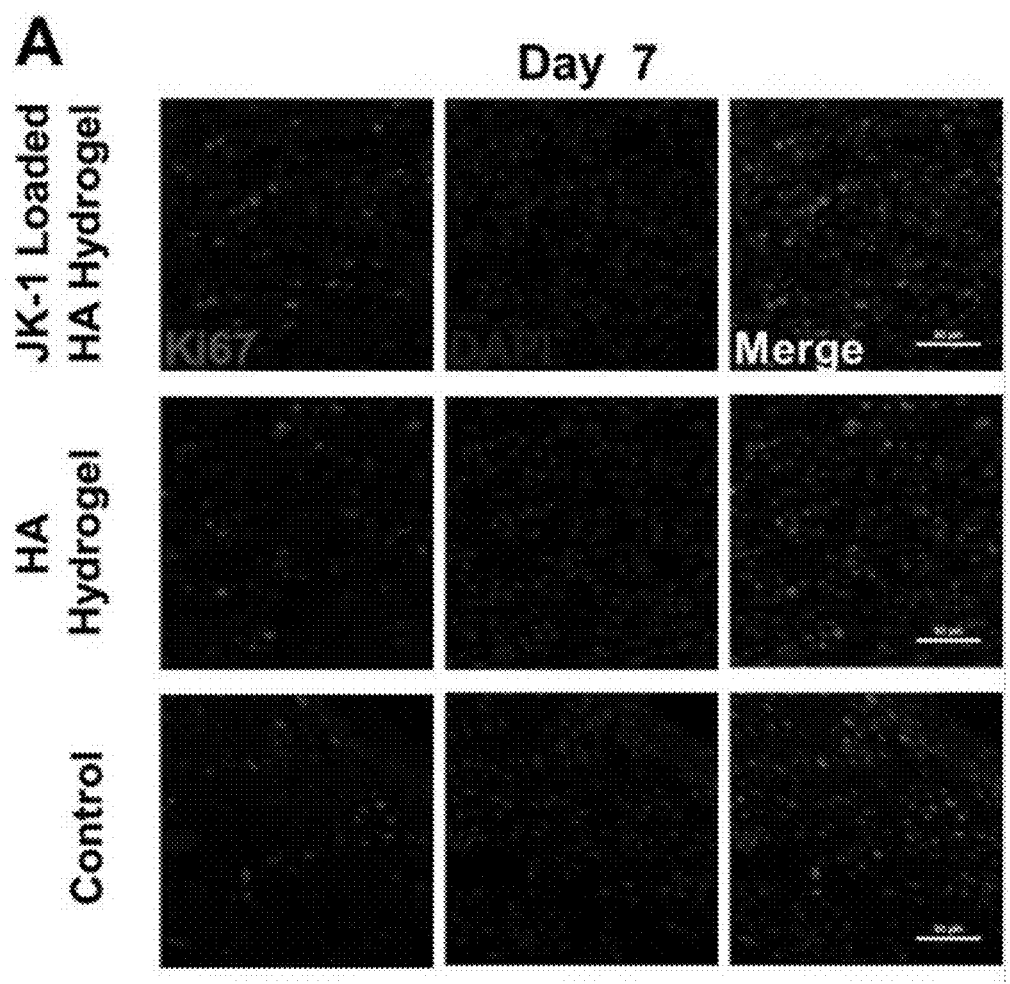
FIG. 12A is a series of immunostained images showing the upregulation of Ki67 expression when using a JK-1-loaded hyaluronic acid hydrogel compared to a hyaluronic acid hydrogel and a control hydrogel.
Figure 12B:
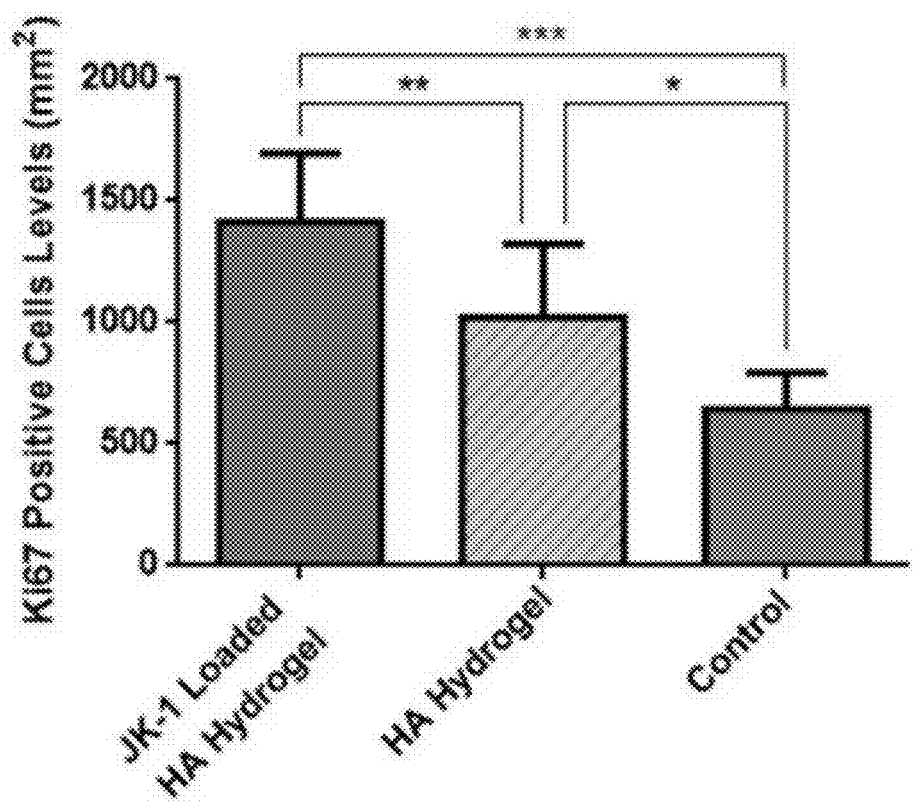
FIG. 12B is a graph comparing the number of Ki67 positives cells levels ($mm^2$) for a JK-1-loaded hyaluronic acid hydrogel, a hyaluronic acid hydrogel, and a control hydrogel
Figure 13A:
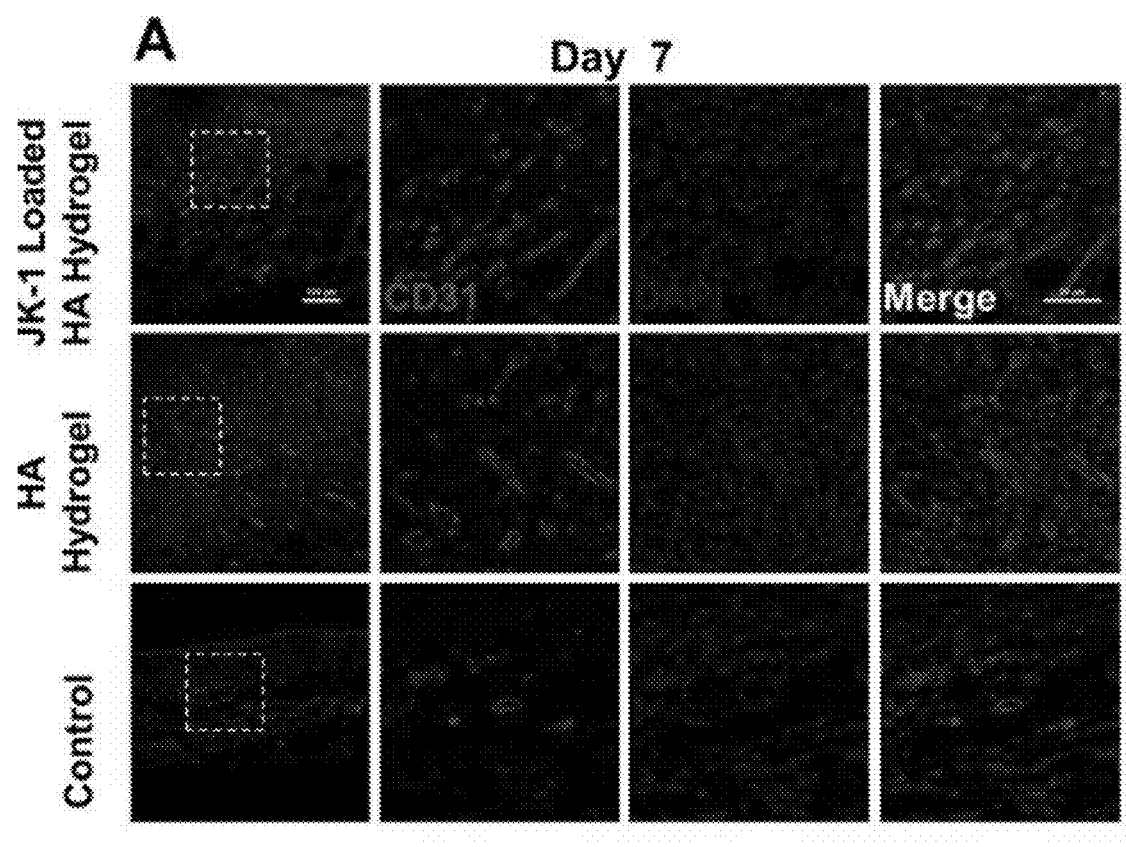
FIG. 13A is a series of immunostained images showing the upregulation of CD31 expression when using a JK-1-loaded hyaluronic acid hydrogel compared to a hyaluronic acid hydrogel and a control hydrogel.
Figure 13B:
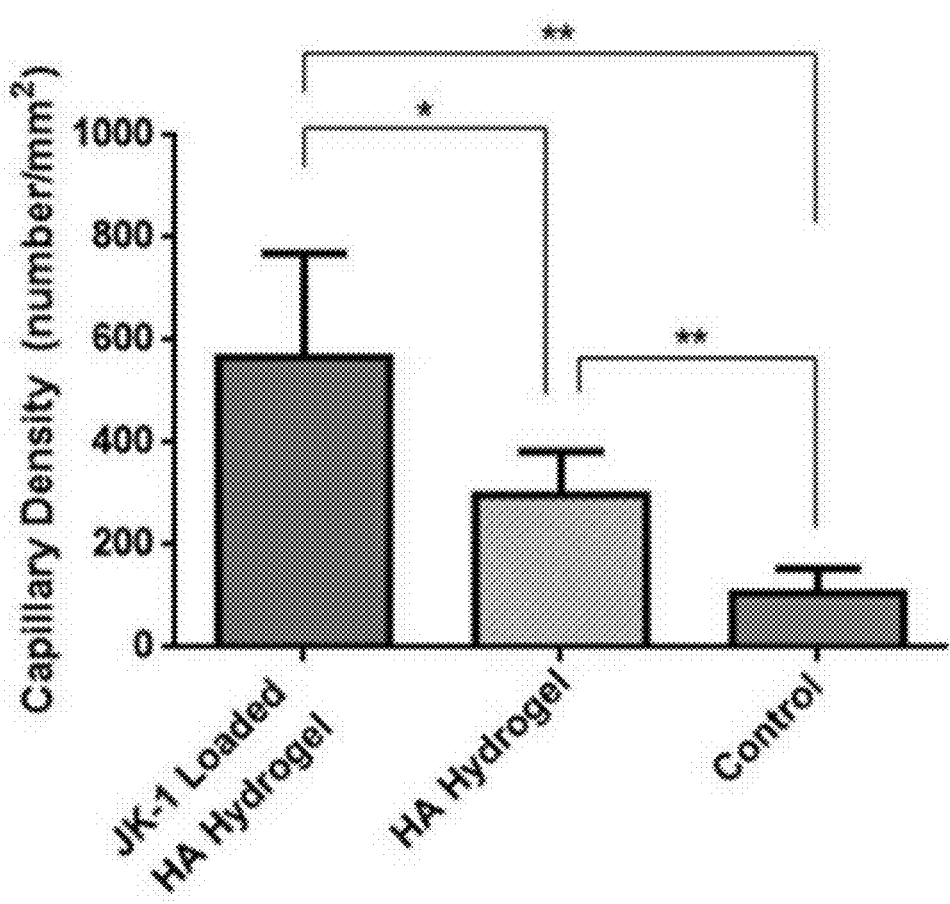
FIG. 13B is a series of immunostained images showing the upregulation of CD31 expression when using a JK-1-loaded hyaluronic acid hydrogel compared to a hyaluronic acid hydrogel and a control hydrogel.

The Ki67 is a marker protein that is associated with cellular proliferation. On day 7, the Ki67 positive cell levels of wounds treated with the HA/JK-1 hydrogel was significantly higher than that of wounds treated with the HA hydrogel, indicating improved cell proliferation due to H₂S release, as shown in the series of images in FIG. 12A and graphically depicted in FIG. 12B. Furthermore, higher immunofluorescence of CD 31 expressions toward wounds treated with the HA/JK-1 hydrogel compared with that of wounds treated with the HA hydrogel demonstrated increased vascularization toward the wound due to the positive effect of H₂S release from the HA/JK-1 hydrogel, as shown in the series of images in FIG. 13A and graphically depicted in FIG. 13B. Thus, it is shown that the specific release of H₂S from the HA/JK-1 hydrogel up-regulates the expressions of CSE and enhances the proangiogenesis of the wound by regulating the expressions of CSE, leading to improved wound regeneration due at least in part to the increase in M2 type macrophage facilitated by the H₂S release from the HA/JK-1 hydrogel. In summary, the HA/JK-1 hydrogel demonstrated significantly improved wound recovery efficiency on granulation tissue formation along with wound re-epithelialization and collagen deposition, as well as neovascularization due to its release of H₂S.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:
1. A wound dressing comprising:
    a biodegradable scaffold material; and
    a hydrogen sulfide donor, wherein the hydrogen sulfide donor is present in the wound dressing in an amount ranging from about 0.5 millimolar to about 150 millimolar.
2. The wound dressing of claim 1, wherein the hydrogen sulfide donor comprises JK-1 having the following structure:

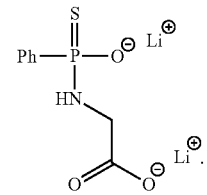

3. The wound dressing of claim 1, wherein the wound dressing releases hydrogen sulfide when introduced into an environment having a pH ranging from 5.0 to 7.0.
4. The wound dressing of claim 1, wherein the wound dressing releases hydrogen sulfide for a time period of up to 75 hours.
5. The wound dressing of claim 1, wherein the wound dressing releases hydrogen sulfide at a concentration ranging from 5 micromolar (μM) to 50 μM.
6. The wound dressing of claim 1, wherein the biodegradable scaffold material comprises a biodegradable polymer, sodium alginate, hyaluronic acid, or a combination thereof.
7. The wound dressing of claim 6, wherein the biodegradable polymer comprises polycaprolactone, polylactic acid, polyglycolic acid, or a combination thereof.
8. The wound dressing of claim 1, wherein the biodegradable scaffold material comprises a nanofibrous scaffold, a sponge, or a hydrogel.
9. The wound dressing of claim 8, wherein the nanofibrous scaffold is an electrospun nanofibrous scaffold.
10. The wound dressing of claim 1, wherein the biodegradable scaffold material is crosslinked.
11. The wound dressing of claim 1, wherein wound dressing increases the production of CD31 and Ki67 from a wound.
12. A method of treating a wound, the method comprising:
    applying a wound dressing to an area of skin encompassing the wound; and
    leaving the wound dressing on the area of skin for a time period ranging up to about 75 hours, wherein the wound dressing comprises a biodegradable scaffold material and a hydrogen sulfide donor, wherein the hydrogen sulfide donor is present in the wound dressing in an amount ranging from about 0.5 millimolar to about 150 millimolar.
13. The method of claim 12, wherein the hydrogen sulfide donor comprises JK-1 having the following structure:

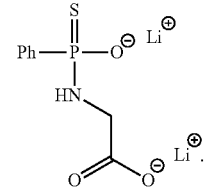 [SMILES: O=C([O-])CNP([O-])(=S)c1ccccc1 ; [Li+] ; [Li+]]

14. The method of claim 12, wherein the wound dressing releases hydrogen sulfide when introduced into an environment having a pH ranging from about 5.0 to about 7.0.

15. The method of claim 12, wherein the wound dressing releases hydrogen sulfide at a concentration ranging from about 5 micromolar (μM) to about 50 μM.

16. The method of claim 12, wherein the biodegradable scaffold material comprises a biodegradable polymer, sodium alginate, hyaluronic acid, or a combination thereof.

17. The method of claim 16, wherein the biodegradable polymer comprises polycaprolactone, polylactic acid, polyglycolic acid, or a combination thereof.

18. The method of claim 12, wherein the biodegradable scaffold material comprises a nanofibrous scaffold, a sponge, or a hydrogel.

19. The method of claim 18, wherein the nanofibrous scaffold is an electrospun nanofibrous scaffold.

20. The method of claim 12, wherein treating the wound with the wound dressing increases the production of CD31 and Ki67 from the wound.

\* \* \* \* \*